(12) United States Patent
Floch et al.

(10) Patent No.: US 8,900,817 B2
(45) Date of Patent: Dec. 2, 2014

(54) PROGASTRIN AND LIVER PATHOLOGIES

(75) Inventors: Jean-François Floch, Sète (FR); Leïla Houhou, Montpellier (FR)

(73) Assignee: Les Laboratories Servier, Suresnes (FR)

(*) Notice: Subject to any disclaimer, the term of this patent is extended or adjusted under 35 U.S.C. 154(b) by 113 days.

(21) Appl. No.: 12/984,507

(22) Filed: Jan. 4, 2011

(65) Prior Publication Data

US 2011/0229488 A1 Sep. 22, 2011

Related U.S. Application Data

(60) Provisional application No. 61/293,557, filed on Jan. 8, 2010.

(51) Int. Cl.
| | | |
|---|---|---|
| *G01N 33/48* | (2006.01) | |
| *G01N 33/53* | (2006.01) | |
| *G01N 33/574* | (2006.01) | |
| *G01N 33/576* | (2006.01) | |
| *G01N 33/577* | (2006.01) | |
| *G01N 33/58* | (2006.01) | |
| *G01N 33/74* | (2006.01) | |

(52) U.S. Cl.
CPC ............ *G01N 33/74* (2013.01); *G01N 2800/50* (2013.01); *G01N 2333/595* (2013.01); *G01N 33/57438* (2013.01); *G01N 33/5767* (2013.01); *G01N 2800/085* (2013.01); *G01N 2800/56* (2013.01)
USPC ................ 435/7.1; 435/7.9; 435/7.92; 435/8; 530/387.1; 530/387.3; 530/388.1; 530/388.15; 530/388.24

(58) Field of Classification Search
None
See application file for complete search history.

(56) References Cited

U.S. PATENT DOCUMENTS

| | | | |
|---|---|---|---|
| 2003/0091574 A1 | 5/2003 | Gevas | |
| 2005/0187152 A1* | 8/2005 | Gevas et al. | .................... 514/12 |
| 2007/0248608 A1* | 10/2007 | Grimes | ....................... 424/142.1 |
| 2011/0117086 A1 | 5/2011 | Pannequin et al. | |
| 2012/0020961 A1 | 1/2012 | Houhou et al. | |

FOREIGN PATENT DOCUMENTS

| | | |
|---|---|---|
| WO | WO 2011/045080 A3 | 4/2011 |
| WO | WO 2012/013609 A1 | 2/2012 |

OTHER PUBLICATIONS http://www.health-nexus.com/liver_diseases.htm, accessed Jul. 31, 2012.*
Siddeshwar et al. (2001, Gut 48:47-52).*
Konturek et al. (2003, Digestion 68:169-177).*
Caplin et al. (1999, J. Hepatology 30:519-526).*
Rengifo-Cam et al., 2004, "Role of Progastrins and Gastrins and Their Receptors in GI and Pancreatic Cancers: Targets for Treatment," *Curr. Pharm. Des.* vol. 10:2345-2358.
Konturek et al., 2003, "Progastrin and Its Products From Patients With Chronic Viral Hepatitis and Liver Cirrhosis," *Scandinavian Journal of Gastroenterology* 38(6):643-647.
Konturek et al., 2002, "Plasma Progastrin and Leptin in Type B and C Viral Hepatitis and Liver Cirrhosis," *Gastroenterology* 122(4):A-306 (Suppl. 1).
PCT International Search Report and Written Opinion of the International Searching Authority from related International Application No. PCT/EP2011/000047 dated Mar. 1, 2011.
Caplin et al., 2000, "Expression and Processing of Gastrin in Pancreatic Adenocarcinoma," *British Journal of Surgery* 87(8):1035-1040.

* cited by examiner

*Primary Examiner* — Elizabeth C Kemmerer
(74) *Attorney, Agent, or Firm* — Dechert LLP

(57) ABSTRACT

Progastrin levels are determined to diagnose one or more liver pathologies.

31 Claims, 40 Drawing Sheets

FIG. 1

Preprogastrin:
SEQ ID NO:100

```
M QRLCVYVLIF ALALAAFSEA SWKPRSQQPD APLGTGANRD LELPWLEQQG
-21           -11           -1 +1           11            21
PASHHRRQLG PQGPPHLVAD PSKKQGPWLE EEEEAYGWMD FGRRSAEDEN
 31         41          51          61          71
```

Progastrin:
SEQ ID NO:101

```
                                  SWKPRSQQPD APLGTGANRD LELPWLEQQG
                                  +1           11           21
PASHHRRQLG PQGPPHLVAD PSKKQGPWLE EEEEAYGWMD FGRRSAEDEN
 31         41          51          61          71
```

G34:
SEQ ID NO:102

```
       QLG PQGPPHLVAD PSKKQGPWLE EEEEAYGWMD F-NH2
            41          51          61        71
```

G34-Gly:
SEQ ID NO:103

```
       QLG PQGPPHLVAD PSKKQGPWLE EEEEAYGWMD FG
            41          51          61        71
```

G17:
SEQ ID NO:104

```
                       QGPWLE EEEEAYGWMD F-NH2
                        51       61        71
```

G17-Gly:
SEQ ID NO:105

```
                       QGPWLE EEEEAYGWMD FG
                        51       61        71
```

CTFP:
SEQ ID NO:106

```
                                            SAEDEN
                                             75
```

FIG. 3A mV$_H$ MAb3

```
gag gtt cag ctc cag cag tct ggg act gtg ctg gca agg cct ggg gct    48
Glu Val Gln Leu Gln Gln Ser Gly Thr Val Leu Ala Arg Pro Gly Ala
1               5                   10                  15 tcc gtg aag atg tcc tgc aag gct tct ggc tac atc ttt acc agc tac    96
Ser Val Lys Met Ser Cys Lys Ala Ser Gly Tyr Ile Phe Thr Ser Tyr
            20                  25                  30 tgg gta cac tgg gtt aaa cag agg cct gga cag ggt cta gaa tgg att   144
Trp Val His Trp Val Lys Gln Arg Pro Gly Gln Gly Leu Glu Trp Ile
        35                  40                  45 ggt ggt ttt tat cct gga aat agt gat tct agg tac aac cag aaa ttc   192
Gly Gly Phe Tyr Pro Gly Asn Ser Asp Ser Arg Tyr Asn Gln Lys Phe
    50                  55                  60 aag ggc aag gcc aca ctg act gca gtc aca tcc gcc agt act gcc tac   240
Lys Gly Lys Ala Thr Leu Thr Ala Val Thr Ser Ala Ser Thr Ala Tyr
65                  70                  75                  80 atg gac ctc agc agc ctg aca aat gag gac tct gcg gtc tat ttc tgt   288
Met Asp Leu Ser Ser Leu Thr Asn Glu Asp Ser Ala Val Tyr Phe Cys
                85                  90                  95 aca aga aga gat agt ccc cag tac tgg ggc caa ggc acc act ctc aca   336
Thr Arg Arg Asp Ser Pro Gln Tyr Trp Gly Gln Gly Thr Thr Leu Thr
                100                 105                 110 gtc tcc tca                                                        345
Val Ser Ser
        115
```

FIG. 3B mV$_L$ MAb3

```
gat gtt ttg atg acc caa act cca ctc tcc ctg cct gtc agt ctt gga    48
Asp Val Leu Met Thr Gln Thr Pro Leu Ser Leu Pro Val Ser Leu Gly
1               5                   10                  15 gat caa gcc tcc atc tct tgc aga tct agt cag agc att gta cat agt    96
Asp Gln Ala Ser Ile Ser Cys Arg Ser Ser Gln Ser Ile Val His Ser
                20                  25              30 aat gga aac acc tat tta gaa tgg tac ctg cag aaa cca ggc cag tct   144
Asn Gly Asn Thr Tyr Leu Glu Trp Tyr Leu Gln Lys Pro Gly Gln Ser
            35                  40                  45 cca aag ctc ctg atc tac aaa gtt tcc aac cga ttt tct ggg gtc cca   192
Pro Lys Leu Leu Ile Tyr Lys Val Ser Asn Arg Phe Ser Gly Val Pro
        50                  55                  60 gac agg ttc agt ggc agt gga tca ggg aca gat ttc aca ctc aag atc   240
Asp Arg Phe Ser Gly Ser Gly Ser Gly Thr Asp Phe Thr Leu Lys Ile
65                  70                  75                  80 agc aga ctg gag gct gag gat ctg gga gtt tat tac tgc ttt caa ggt   288
Ser Arg Leu Glu Ala Glu Asp Leu Gly Val Tyr Tyr Cys Phe Gln Gly
                85                  90                  95 tca cat gtt ccg ttc acg ttc gga ggg ggg acc aag ctg gaa ata aaa   336
Ser His Val Pro Phe Thr Phe Gly Gly Gly Thr Lys Leu Glu Ile Lys
                100                 105                 110
```

FIG. 3C mV$_H$ MAb4

```
cag gtt cag ttg cag cag tct gga gct gag ctg atg aag cca ggg gcc    48
Gln Val Gln Leu Gln Gln Ser Gly Ala Glu Leu Met Lys Pro Gly Ala
1               5                   10                  15 tca gtg aag ata tcc tgc aag gct act ggc tac aca ttc agt agc tcc    96
Ser Val Lys Ile Ser Cys Lys Ala Thr Gly Tyr Thr Phe Ser Ser Ser
                20                  25                  30 tgg ata gag tgg tta aaa cag agg cct gga cat ggc ctt gag tgg att   144
Trp Ile Glu Trp Leu Lys Gln Arg Pro Gly His Gly Leu Glu Trp Ile
        35                  40                  45 gga gag ttt tta cct gga agt ggt agt aca gac tac aat gag aag ttc   192
Gly Glu Phe Leu Pro Gly Ser Gly Ser Thr Asp Tyr Asn Glu Lys Phe
        50                  55                  60 aag ggc aag gcc aca ttc act gca gac aca tcc tcc gac aca gcc tac   240
Lys Gly Lys Ala Thr Phe Thr Ala Asp Thr Ser Ser Asp Thr Ala Tyr
65                  70                  75                  80 atg cta ctc agc agc ctg aca tct gag gac tct gcc gtc tat tac tgt   288
Met Leu Leu Ser Ser Leu Thr Ser Glu Asp Ser Ala Val Tyr Tyr Cys
                85                  90                  95 gca act gat ggt aat tat gac tgg ttt gct tac tgg ggc caa ggg act   336
Ala Thr Asp Gly Asn Tyr Asp Trp Phe Ala Tyr Trp Gly Gln Gly Thr
                100                 105                 110 ctg gtc act gtc tct gca                                            354
Leu Val Thr Val Ser Ala
            115
```

FIG. 3D mV$_L$ MAb4

```
gat ctt gtg atg acc caa act cca ctc tcc ctg cct gtc agt ctt gga    48
Asp Leu Val Met Thr Gln Thr Pro Leu Ser Leu Pro Val Ser Leu Gly
1               5               10              15 gat caa gcc tcc atc tct tgc aga tct agt cag agc ctt gta cac agt    96
Asp Gln Ala Ser Ile Ser Cys Arg Ser Ser Gln Ser Leu Val His Ser
                20              25              30 agt gga gtc acc tat tta cat tgg tac ctg cag aag cca ggc cag tct   144
Ser Gly Val Thr Tyr Leu His Trp Tyr Leu Gln Lys Pro Gly Gln Ser
            35              40              45 cca aag ctc ctg atc tac aaa gtt tcc aac cga ttt tct ggg gtc cca   192
Pro Lys Leu Leu Ile Tyr Lys Val Ser Asn Arg Phe Ser Gly Val Pro
        50              55              60 gac agg ttc agt ggc agt gga tca ggg aca gat ttc aca ctc aag atc   240
Asp Arg Phe Ser Gly Ser Gly Ser Gly Thr Asp Phe Thr Leu Lys Ile
65              70              75              80 agc aga gtg gag gct gag gat ctg gga gtt tat ttc tgc tct caa agt   288
Ser Arg Val Glu Ala Glu Asp Leu Gly Val Tyr Phe Cys Ser Gln Ser
                85              90              95 aca cat gtt cct ccc acg ttc ggc tcg ggg aca aag ttg gaa ata aaa   336
Thr His Val Pro Pro Thr Phe Gly Ser Gly Thr Lys Leu Glu Ile Lys
            100             105             110
```

FIG. 3E mV$_H$ MAb8

| | | | | | | | | | | | | | | | | |
|---|---|---|---|---|---|---|---|---|---|---|---|---|---|---|---|---|
| gaa | gtg | cag | ctg | gtg | gag | tct | ggg | gga | ggc | tta | gtg | aag | cct | gga | ggg | 48 |
| Glu | Val | Gln | Leu | Val | Glu | Ser | Gly | Gly | Gly | Leu | Val | Lys | Pro | Gly | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tcc | ctg | aaa | ctc | tcc | tgt | gca | gcc | tct | gga | ttc | act | ttc | act | acc | tat | 96 |
| Ser | Leu | Lys | Leu | Ser | Cys | Ala | Ala | Ser | Gly | Phe | Thr | Phe | Thr | Thr | Tyr | |
| | | | 20 | | | | | 25 | | | | | 30 | | | |

| | | | | | | | | | | | | | | | | |
|---|---|---|---|---|---|---|---|---|---|---|---|---|---|---|---|---|
| gcc | atg | tct | tgg | gtt | cgc | cag | act | ccg | gag | aag | agg | ctg | gag | tgg | gtc | 144 |
| Ala | Met | Ser | Trp | Val | Arg | Gln | Thr | Pro | Glu | Lys | Arg | Leu | Glu | Trp | Val | |
| | | 35 | | | | | 40 | | | | | 45 | | | | |

| | | | | | | | | | | | | | | | | |
|---|---|---|---|---|---|---|---|---|---|---|---|---|---|---|---|---|
| gca | acc | att | agt | agt | ggt | ggt | act | tac | acc | tac | tat | cca | gac | agt | gtg | 192 |
| Ala | Thr | Ile | Ser | Ser | Gly | Gly | Thr | Tyr | Thr | Tyr | Tyr | Pro | Asp | Ser | Val | |
| | 50 | | | | | 55 | | | | | 60 | | | | | |

| | | | | | | | | | | | | | | | | |
|---|---|---|---|---|---|---|---|---|---|---|---|---|---|---|---|---|
| aag | ggt | cga | ttc | acc | atc | tcc | aga | gac | aat | gcc | aag | aac | gcc | cta | tac | 240 |
| Lys | Gly | Arg | Phe | Thr | Ile | Ser | Arg | Asp | Asn | Ala | Lys | Asn | Ala | Leu | Tyr | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ctg | caa | atg | agc | agt | ctg | agg | tct | gag | gac | acg | gcc | atg | tat | tac | tgt | 288 |
| Leu | Gln | Met | Ser | Ser | Leu | Arg | Ser | Glu | Asp | Thr | Ala | Met | Tyr | Tyr | Cys | |
| | | | | 85 | | | | | 90 | | | | | 95 | | |

| | | | | | | | | | | | | | | | | |
|---|---|---|---|---|---|---|---|---|---|---|---|---|---|---|---|---|
| gca | aca | cag | ggg | aat | tac | tct | ttg | gac | ttc | tgg | ggc | caa | ggc | acc | tct | 336 |
| Ala | Thr | Gln | Gly | Asn | Tyr | Ser | Leu | Asp | Phe | Trp | Gly | Gln | Gly | Thr | Ser | |
| | | | 100 | | | | | 105 | | | | | 110 | | | |

| | | | | |
|---|---|---|---|---|
| ctc | aca | gtc | tcc | tca | 351 |
| Leu | Thr | Val | Ser | Ser | |
| | | 115 | | | |

FIG. 3F mV$_L$ MAb8

```
gac att gtg atg acg cag gct gca tcc tct aat cca gtc act ctt gga    48
Asp Ile Val Met Thr Gln Ala Ala Ser Ser Asn Pro Val Thr Leu Gly
1               5                   10                  15 aca tcc gct tcc atc tcc tgc agg tct agt aag agt ctc cga cat act    96
Thr Ser Ala Ser Ile Ser Cys Arg Ser Ser Lys Ser Leu Arg His Thr
                20                  25                  30 aaa ggc atc act ttt ttg tat tgg tat ctg cag aag cca ggc cag tct   144
Lys Gly Ile Thr Phe Leu Tyr Trp Tyr Leu Gln Lys Pro Gly Gln Ser
            35                  40                  45 cct cag ctc ctg att tat cag atg tcc aac ctt gcc tca gga gtc cca   192
Pro Gln Leu Leu Ile Tyr Gln Met Ser Asn Leu Ala Ser Gly Val Pro
        50                  55                  60 gac agg ttc agt agc agt ggg tca gga act gat ttc aca ctg aga atc   240
Asp Arg Phe Ser Ser Ser Gly Ser Gly Thr Asp Phe Thr Leu Arg Ile
65                  70                  75                  80 agc aga gtg gag gct gag gat ttg ggt gtt tat tac tgt gct caa aat   288
Ser Arg Val Glu Ala Glu Asp Leu Gly Val Tyr Tyr Cys Ala Gln Asn
                85                  90                  95 cta gaa ctt ccg ctc acg ttc ggt gct ggg acc aag ctg gag ctg aaa   336
Leu Glu Leu Pro Leu Thr Phe Gly Ala Gly Thr Lys Leu Glu Leu Lys
                100                 105                 110
```

FIG. 3G mV$_H$ MAb13

| | | | | | | | | | | | | | | | | |
|---|---|---|---|---|---|---|---|---|---|---|---|---|---|---|---|---|
| gag | gtg | cag | ctg | gtg | gag | tct | ggg | gga | ggc | ttg | gtg | cag | cct | gga | ggg | 48 |
| Glu | Val | Gln | Leu | Val | Glu | Ser | Gly | Gly | Gly | Leu | Val | Gln | Pro | Gly | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tcc | ctg | aaa | ctc | tcc | tgt | gca | gcc | tct | gga | ttc | att | ttc | agt | agc | tat | 96 |
| Ser | Leu | Lys | Leu | Ser | Cys | Ala | Ala | Ser | Gly | Phe | Ile | Phe | Ser | Ser | Tyr | |
| | | 20 | | | | | 25 | | | | | 30 | | | | |

| | | | | | | | | | | | | | | | | |
|---|---|---|---|---|---|---|---|---|---|---|---|---|---|---|---|---|
| ggc | atg | tct | tgg | gtt | cgc | cag | tct | cca | gac | agg | agg | ctg | gag | ttg | gtc | 144 |
| Gly | Met | Ser | Trp | Val | Arg | Gln | Ser | Pro | Asp | Arg | Arg | Leu | Glu | Leu | Val | |
| | | 35 | | | | | 40 | | | | | 45 | | | | |

| | | | | | | | | | | | | | | | | |
|---|---|---|---|---|---|---|---|---|---|---|---|---|---|---|---|---|
| gca | agt | att | aat | act | ttt | ggt | gat | aga | acc | tat | tat | cca | gac | agt | gtg | 192 |
| Ala | Ser | Ile | Asn | Thr | Phe | Gly | Asp | Arg | Thr | Tyr | Tyr | Pro | Asp | Ser | Val | |
| | 50 | | | | | 55 | | | | | 60 | | | | | |

| | | | | | | | | | | | | | | | | |
|---|---|---|---|---|---|---|---|---|---|---|---|---|---|---|---|---|
| aag | ggc | cga | ttc | acc | atc | tcc | aga | gac | aat | gcc | aag | aac | acc | ctg | tac | 240 |
| Lys | Gly | Arg | Phe | Thr | Ile | Ser | Arg | Asp | Asn | Ala | Lys | Asn | Thr | Leu | Tyr | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ctg | caa | atg | acc | agt | ctg | aag | tct | gag | gac | aca | gcc | att | tat | tac | tgt | 288 |
| Leu | Gln | Met | Thr | Ser | Leu | Lys | Ser | Glu | Asp | Thr | Ala | Ile | Tyr | Tyr | Cys | |
| | | | | 85 | | | | | 90 | | | | | 95 | | |

| | | | | | | | | | | | | | | | | |
|---|---|---|---|---|---|---|---|---|---|---|---|---|---|---|---|---|
| gca | aga | ggg | acc | gga | acc | tac | tgg | ggc | caa | ggc | acc | act | ctc | aca | gtc | 336 |
| Ala | Arg | Gly | Thr | Gly | Thr | Tyr | Trp | Gly | Gln | Gly | Thr | Thr | Leu | Thr | Val | |
| | | | 100 | | | | | 105 | | | | 110 | | | | |

| | | | |
|---|---|---|---|
| tcc | tca | | 342 |
| Ser | Ser | | |

FIG. 3H mV$_L$ MAb13

| | | | | | | | | | | | | | | | | |
|---|---|---|---|---|---|---|---|---|---|---|---|---|---|---|---|---|
| gat | gtt | gtg | ctg | acc | cag | act | cca | ctc | act | ttg | tcg | gtt | acc | att | gga | 48 |
| Asp | Val | Val | Leu | Thr | Gln | Thr | Pro | Leu | Thr | Leu | Ser | Val | Thr | Ile | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| caa | cca | gcc | tcc | atc | tcc | tgc | aag | tca | agt | cag | agc | ctc | tta | gat | agt | 96 |
| Gln | Pro | Ala | Ser | Ile | Ser | Cys | Lys | Ser | Ser | Gln | Ser | Leu | Leu | Asp | Ser | |
| | | | 20 | | | | | 25 | | | | | 30 | | | |

| | | | | | | | | | | | | | | | | |
|---|---|---|---|---|---|---|---|---|---|---|---|---|---|---|---|---|
| gat | gga | aag | aca | tat | ttg | aat | tgg | ttg | tta | cag | agg | cca | ggc | cag | tct | 144 |
| Asp | Gly | Lys | Thr | Tyr | Leu | Asn | Trp | Leu | Leu | Gln | Arg | Pro | Gly | Gln | Ser | |
| | | 35 | | | | | 40 | | | | | 45 | | | | |

| | | | | | | | | | | | | | | | | |
|---|---|---|---|---|---|---|---|---|---|---|---|---|---|---|---|---|
| cca | aag | cgc | cta | atc | tat | ctg | gtg | tct | aaa | ctg | gac | tct | gga | gtc | cct | 192 |
| Pro | Lys | Arg | Leu | Ile | Tyr | Leu | Val | Ser | Lys | Leu | Asp | Ser | Gly | Val | Pro | |
| | 50 | | | | | | 55 | | | | | 60 | | | | |

| | | | | | | | | | | | | | | | | |
|---|---|---|---|---|---|---|---|---|---|---|---|---|---|---|---|---|
| gac | agg | ttc | act | ggc | agt | gga | tca | ggg | aca | gat | ttc | aca | ctg | aaa | atc | 240 |
| Asp | Arg | Phe | Thr | Gly | Ser | Gly | Ser | Gly | Thr | Asp | Phe | Thr | Leu | Lys | Ile | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| agc | aga | gtg | gag | gct | gag | gat | ttg | gga | gtt | tat | tat | tgc | tgg | caa | ggt | 288 |
| Ser | Arg | Val | Glu | Ala | Glu | Asp | Leu | Gly | Val | Tyr | Tyr | Cys | Trp | Gln | Gly | |
| | | | | 85 | | | | | 90 | | | | | 95 | | |

| | | | | | | | | | | | | | | | | |
|---|---|---|---|---|---|---|---|---|---|---|---|---|---|---|---|---|
| aca | cat | ttt | cct | cag | acg | ttc | ggt | gga | ggc | acc | aag | ctg | gaa | atc | aaa | 336 |
| Thr | His | Phe | Pro | Gln | Thr | Phe | Gly | Gly | Gly | Thr | Lys | Leu | Glu | Ile | Lys | |
| | | | 100 | | | | | 105 | | | | | 110 | | | |

FIG. 3I mV$_H$ MAb16

| | | | | | | | | | | | | | | | | |
|---|---|---|---|---|---|---|---|---|---|---|---|---|---|---|---|---|
| cag | gtc | caa | ctg | cag | cag | tct | ggg | gct | gaa | ctg | gtg | aag | cct | ggg | gct | 48 |
| Gln | Val | Gln | Leu | Gln | Gln | Ser | Gly | Ala | Glu | Leu | Val | Lys | Pro | Gly | Ala | |
| 1 | | | 5 | | | | | | 10 | | | | | 15 | | |

| | | | | | | | | | | | | | | | | |
|---|---|---|---|---|---|---|---|---|---|---|---|---|---|---|---|---|
| tca | gtg | aag | ttg | tcc | tgc | aag | gct | tct | ggc | tac | acc | ttc | acc | agc | tac | 96 |
| Ser | Val | Lys | Leu | Ser | Cys | Lys | Ala | Ser | Gly | Tyr | Thr | Phe | Thr | Ser | Tyr | |
| | | 20 | | | | | 25 | | | | | 30 | | | | |

| | | | | | | | | | | | | | | | | |
|---|---|---|---|---|---|---|---|---|---|---|---|---|---|---|---|---|
| tat | atg | tac | tgg | gtg | aag | cag | agg | cct | gga | caa | ggc | ctt | gag | tgg | att | 144 |
| Tyr | Met | Tyr | Trp | Val | Lys | Gln | Arg | Pro | Gly | Gln | Gly | Leu | Glu | Trp | Ile | |
| | | 35 | | | | | 40 | | | | | 45 | | | | |

| | | | | | | | | | | | | | | | | |
|---|---|---|---|---|---|---|---|---|---|---|---|---|---|---|---|---|
| gga | gag | att | aat | cct | agc | aat | ggt | ggt | act | aac | ttc | aat | gag | aag | ttc | 192 |
| Gly | Glu | Ile | Asn | Pro | Ser | Asn | Gly | Gly | Thr | Asn | Phe | Asn | Glu | Lys | Phe | |
| | 50 | | | | | 55 | | | | | | 60 | | | | |

| | | | | | | | | | | | | | | | | |
|---|---|---|---|---|---|---|---|---|---|---|---|---|---|---|---|---|
| aag | agc | aag | gcc | aca | ctg | act | gta | gac | aaa | tcc | tcc | agc | aca | gca | tac | 240 |
| Lys | Ser | Lys | Ala | Thr | Leu | Thr | Val | Asp | Lys | Ser | Ser | Ser | Thr | Ala | Tyr | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| atg | caa | ctc | agc | agc | ctg | aca | tct | gag | gac | tct | gcg | gtc | tat | tac | tgt | 288 |
| Met | Gln | Leu | Ser | Ser | Leu | Thr | Ser | Glu | Asp | Ser | Ala | Val | Tyr | Tyr | Cys | |
| | | | | 85 | | | | | 90 | | | | | 95 | | |

| | | | | | | | | | | | | | | | | |
|---|---|---|---|---|---|---|---|---|---|---|---|---|---|---|---|---|
| aca | aga | ggc | ggt | tac | tac | ccc | ttt | gac | tac | tgg | ggc | caa | ggc | acc | act | 336 |
| Thr | Arg | Gly | Gly | Tyr | Tyr | Pro | Phe | Asp | Tyr | Trp | Gly | Gln | Gly | Thr | Thr | |
| | | | 100 | | | | | 105 | | | | | 110 | | | |

| | | | | | |
|---|---|---|---|---|---|
| ctc | aca | gtc | tcc | tca | 351 |
| Leu | Thr | Val | Ser | Ser | |
| | | 115 | | | |

FIG. 3J mV$_L$ MAb16

```
gat gtt gtg atg acc cag act cca ctc act ttg tcg gtt acc att ggg   48
Asp Val Val Met Thr Gln Thr Pro Leu Thr Leu Ser Val Thr Ile Gly
1               5                   10                  15 cgc cca gcc tcc atc tct tgc aag tca agt cag agc ctc tta gac agt   96
Arg Pro Ala Ser Ile Ser Cys Lys Ser Ser Gln Ser Leu Leu Asp Ser
                20                  25              30 gat gga aag aca tat ttg tat tgg ttg tta cag agg cca ggc cag tct   144
Asp Gly Lys Thr Tyr Leu Tyr Trp Leu Leu Gln Arg Pro Gly Gln Ser
            35                  40                  45 cca aag cgc cta atc tat ctg gtg tct gag ctg gac tct gga gtc cct   192
Pro Lys Arg Leu Ile Tyr Leu Val Ser Glu Leu Asp Ser Gly Val Pro
        50                  55                  60 gac agg atc act ggc agt ggg tcg ggg aca gat ttc aca ctg aag atc   240
Asp Arg Ile Thr Gly Ser Gly Ser Gly Thr Asp Phe Thr Leu Lys Ile
65                  70                  75                  80 agc aga gtg gag gct gag gat ttg gga gtt tat tat tgc tgg caa gga   288
Ser Arg Val Glu Ala Glu Asp Leu Gly Val Tyr Tyr Cys Trp Gln Gly
                85                  90                  95 aca cat tct ccg tac acg ttc gga ggg ggg acc aag ctg gaa ata aaa   336
Thr His Ser Pro Tyr Thr Phe Gly Gly Gly Thr Lys Leu Glu Ile Lys
                100                 105                 110
```

FIG. 3K mV$_H$ MAb19

```
gat gtg cag ctt cag gag tcg gga cct ggc ctg gtg aaa cct tct cag    48
Asp Val Gln Leu Gln Glu Ser Gly Pro Gly Leu Val Lys Pro Ser Gln
1               5                   10                  15 tct ctg tcc ctc aca tgc act gtc act ggc tac tca atc acc agt gat    96
Ser Leu Ser Leu Thr Cys Thr Val Thr Gly Tyr Ser Ile Thr Ser Asp
                20                  25                  30 tat gcc tgg aat tgg atc cgg cag ttt cca gga aac aaa ctg gag tgg   144
Tyr Ala Trp Asn Trp Ile Arg Gln Phe Pro Gly Asn Lys Leu Glu Trp
        35                  40                  45 atg ggc tac ata agc ttc agt ggt tac act agt tac aac cca tct ctc   192
Met Gly Tyr Ile Ser Phe Ser Gly Tyr Thr Ser Tyr Asn Pro Ser Leu
        50                  55                  60 aaa agt cga atc tct gtc act cgg gac aca tcc agg aac caa ttc ttc   240
Lys Ser Arg Ile Ser Val Thr Arg Asp Thr Ser Arg Asn Gln Phe Phe
65                  70                  75                  80 ctc cag ttg act tct gtg act act gag gac aca gcc aca tat tac tgt   288
Leu Gln Leu Thr Ser Val Thr Thr Glu Asp Thr Ala Thr Tyr Tyr Cys
                85                  90                  95 gca aga gag gtc aac tat ggg gac tcc tac cac ttt gac tac tgg ggc   336
Ala Arg Glu Val Asn Tyr Gly Asp Ser Tyr His Phe Asp Tyr Trp Gly
                100                 105                 110 caa ggc acc att gtc aca gtc tcc tca                               363
Gln Gly Thr Ile Val Thr Val Ser Ser
                115                 120
```

FIG. 3L mV$_L$ MAb19

```
caa ctt gcg ctc act cag tca tct tca gcc tct ttc tcc ctg gga gcc    48
Gln Leu Ala Leu Thr Gln Ser Ser Ser Ala Ser Phe Ser Leu Gly Ala
1               5                   10                  15 tca gca aaa cta acg tgc act ttg agt agt caa cac aga acg tac acc    96
Ser Ala Lys Leu Thr Cys Thr Leu Ser Ser Gln His Arg Thr Tyr Thr
            20                  25                  30 att gaa tgg tat cag caa cag tca ctc aag cct cct aag tat gtg atg   144
Ile Glu Trp Tyr Gln Gln Gln Ser Leu Lys Pro Pro Lys Tyr Val Met
        35                  40                  45 gag gtt aag aaa gat gga agc cac agc aca ggt cat ggg att cct gat   192
Glu Val Lys Lys Asp Gly Ser His Ser Thr Gly His Gly Ile Pro Asp
    50                  55                  60 cgc ttc tct gga tcc agt tct ggt gct gat cgc tac ctc agc att tcc   240
Arg Phe Ser Gly Ser Ser Ser Gly Ala Asp Arg Tyr Leu Ser Ile Ser
65                  70                  75                  80 aac atc cag cct gaa gat gaa gca ata tac atc tgt ggt gtg ggt gat   288
Asn Ile Gln Pro Glu Asp Glu Ala Ile Tyr Ile Cys Gly Val Gly Asp
                85                  90                  95 gca att aag gga caa tct gtg ttt gtt ttc ggc ggt ggc acc aag gtc   336
Ala Ile Lys Gly Gln Ser Val Phe Val Phe Gly Gly Gly Thr Lys Val
                    100                 105                 110 act gtc cta                                                       345
Thr Val Leu
            115
```

FIG. 4A hV$_H$ MAb3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Tyr
            20                  25                  30

Trp Val His Trp Val Arg Gln Ala Pro Gly Gln Arg Leu Glu Trp Met
            35                  40                  45

Gly Gly Phe Tyr Pro Gly Asn Ser Asp Ser Arg Tyr Ser Gln Lys Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
            85                  90                  95

Thr Arg Arg Asp Ser Pro Gln Tyr Trp Gly Gln Gly Thr Leu Val Thr
            100                 105                 110

Val Ser Ser
    115

FIG. 4B hV$_L$ MAb3

Asp Val Val Met Thr Gln Ser Pro Leu Ser Leu Pro Val Thr Leu Gly
1            5                10                15

Gln Pro Ala Ser Ile Ser Cys Arg Ser Ser Gln Ser Ile Val His Ser
            20              25                30

Asn Gly Asn Thr Tyr Leu Glu Trp Phe Gln Gln Arg Pro Gly Gln Ser
            35              40              45

Pro Arg Arg Leu Ile Tyr Lys Val Ser Asn Arg Phe Ser Gly Val Pro
       50              55              60

Asp Arg Phe Ser Gly Ser Gly Ser Gly Thr Asp Phe Thr Leu Lys Ile
65              70              75              80

Ser Arg Val Glu Ala Glu Asp Val Gly Val Tyr Tyr Cys Phe Gln Gly
            85              90              95

Ser His Val Pro Phe Thr Phe Gly Gly Gly Thr Lys Val Glu Ile Lys
            100             105             110

FIG. 4C hV$_H$ MAb4

Gln Val Gln Leu Val Gln Ser Gly Ala Glu Val Lys Lys Pro Gly Ala
1               5                       10                          15

Ser Val Lys Val Ser Cys Lys Ala Ser Gly Tyr Thr Phe Ser Ser Ser
                20                      25                          30

Trp Met His Trp Val Arg Gln Ala Pro Gly Gln Gly Leu Glu Trp Met
            35                      40                      45

Gly Ile Phe Leu Pro Gly Ser Gly Ser Thr Asp Tyr Ala Gln Lys Phe
        50                      55                  60

Gln Gly Arg Val Thr Met Thr Arg Asp Thr Ser Thr Ser Thr Val Tyr
65                      70                      75                      80

Met Glu Leu Ser Ser Leu Arg Ser Glu Asp Thr Ala Val Tyr Tyr Cys
                85                      90                      95

Ala Thr Asp Gly Asn Tyr Asp Trp Phe Ala Tyr Trp Gly Gln Gly Thr
                100                         105                     110

Leu Val Thr Val Ser Ser
        115

FIG. 4D hV$_L$ MAb4

Asp Ile Val Met Thr Gln Thr Pro Leu Ser Leu Ser Val Thr Pro Gly
1              5                   10                  15

Gln Pro Ala Ser Ile Ser Cys Lys Ser Ser Gln Ser Leu Val His Ser
            20                  25                  30

Ser Gly Val Thr Tyr Leu Tyr Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
            85                  90                  95

Thr His Val Pro Pro Thr Phe Gly Gln Gly Thr Lys Leu Glu Ile Lys
            100                 105                 110

FIG. 4E hV$_H$ MAb8(a)

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Ser Trp Val Arg Gln Ala Pro Gly Lys Gly Leu Glu Trp Val
            35                  40                  45

Ser Ser Ile Ser Ser Gly Gly Thr Tyr Thr Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
                100                 105                 110

Val Thr Val Ser Ser
            115
```

FIG. 4F hV$_L$ MAb8(a)

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Arg His Thr
                20                  25                  30

Lys Gly Ile Thr Phe Leu Tyr Trp Tyr Leu Gln Lys Pro Gly Gln Ser
            35                  40                  45

Pro Gln Leu Leu Ile Tyr Gln Met Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110
```

FIG. 4G hV$_H$ MAb8(b)

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Asn Trp Val Arg Gln Ala Pro Gly Lys Gly Leu Glu Trp Val
            35                  40                  45

Ser Ser Ile Ser Ser Gly Gly Thr Tyr Thr Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
                100                 105                 110

Val Thr Val Ser Ser
        115

FIG. 4H hV$_L$ MAb8(b)

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Arg His Thr
            20                  25              30

Lys Gly Ile Thr Phe Leu Asp Trp Tyr Leu Gln Lys Pro Gly Gln Ser
            35                  40                  45

Pro Gln Leu Leu Ile Tyr Gln Met Ser Asn Arg Ala Ser Gly Val Pro
        50              55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Ala Gln Asn
            85                  90                  95

Leu Glu Leu Pro Leu Thr Phe Gly Gly Gly Thr Lys Val Glu Ile Lys
            100                 105                 110

FIG. 4I hV$_H$ MAb8(c)

Glu Val Gln Leu Val Glu Ser Gly Gly Gly Leu Val Lys Pro Gly Gly
1           5                   10                  15

Ser Leu Arg Leu Ser Cys Ala Ala Ser Gly Phe Thr Phe Thr Thr Tyr
            20                  25                  30

Ala Met Ser Trp Val Arg Gln Ala Pro Gly Lys Gly Leu Glu Trp Val
            35                  40                  45

Ser Thr Ile Ser Ser Gly Gly Thr Tyr Thr Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
                100                 105                 110

Val Thr Val Ser Ser
        115

FIG. 4J hV$_L$ MAb8(c)

Asp Ile Val Met Thr Gln Ser Pro Leu Ser Leu Pro Val Thr Pro Gly
1              5                   10                  15

Glu Pro Ala Ser Ile Ser Cys Arg Ser Ser Lys Ser Leu Arg His Thr
              20                  25                  30

Lys Gly Ile Thr Phe Leu Tyr Trp Tyr Leu Gln Lys Pro Gly Gln Ser
              35                  40                  45

Pro Gln Leu Leu Ile Tyr Gln Met Ser Asn Arg Ala Ser Gly Val Pro
              50              55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
              85                  90                  95

Leu Glu Leu Pro Leu Thr Phe Gly Gly Gly Thr Lys Val Glu Ile Lys
              100                 105                 110

FIG. 4K hV$_H$ MAb13(a)

Glu Val Gln Leu Val Glu Ser Gly Gly Gly Leu Val Gln Pro Gly Gly
1                    5                        10                       15

Ser Leu Arg Leu Ser Cys Ala Ala Ser Gly Phe Ile Phe Ser Ser Tyr
                20                    25                      30

Gly Met Ser Trp Val Arg Gln Ala Pro Gly Lys Gly Leu Glu Trp Val
            35                    40                       45

Ala Asn Ile Asn Thr Phe Gly Asp Arg Thr Tyr Tyr Val Asp Ser Val
      50                    55                       60

Lys Gly Arg Phe Thr Ile Ser Arg Asp Asn Ala Lys Asn Ser Leu Tyr
65                   70                        75                       80

Leu Gln Met Asn Ser Leu Arg Ala Glu Asp Thr Ala Val Tyr Tyr Cys
                85                        90                       95

Ala Arg Gly Thr Gly Thr Tyr Trp Gly Gln Gly Thr Leu Val Thr Val
                100                      105                      110

Ser Ser

FIG. 4L hV$_L$ MAb13(a)

Asp Val Val Met Thr Gln Ser Pro Leu Ser Leu Pro Val Thr Leu Gly
1              5                   10                  15

Gln Pro Ala Ser Ile Ser Cys Arg Ser Ser Gln Ser Leu Leu Asp Ser
             20                  25                  30

Asp Gly Lys Thr Tyr Leu Asn Trp Phe Gln Gln Arg Pro Gly Gln Ser
         35                  40                  45

Pro Arg Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65              70                  75                      80

Ser Arg Val Glu Ala Glu Asp Val Gly Val Tyr Tyr Cys Trp Gln Gly
            85                  90                  95

Thr His Phe Pro Gln Thr Phe Gly Gly Gly Thr Lys Val Glu Ile Lys
             100                 105                 110

FIG. 4M hV$_H$ MAb13(b)

Glu Val Gln Leu Val Glu Ser Gly Gly Gly Leu Val Gln Pro Gly Gly
1               5                       10                      15

Ser Leu Arg Leu Ser Cys Ala Ala Ser Gly Phe Ile Phe Ser Ser Tyr
            20                  25                      30

Gly Met Ser Trp Val Arg Gln Ala Pro Gly Lys Gly Leu Glu Trp Val
            35                      40                      45

Ala Ser Ile Asn Thr Phe Gly Asp Arg Thr Tyr Tyr Val Asp Ser Val
        50                  55                      60

Lys Gly Arg Phe Thr Ile Ser Arg Asp Asn Ala Lys Asn Ser Leu Tyr
65                      70                      75                      80

Leu Gln Met Asn Ser Leu Arg Ala Glu Asp Thr Ala Val Tyr Tyr Cys
                85                      90                      95

Ala Arg Gly Thr Gly Thr Tyr Trp Gly Gln Gly Thr Leu Val Thr Val
                100                     105                     110

Ser Ser

FIG. 4N hV<sub>L</sub> MAb13(b)

Asp Val Val Met Thr Gln Ser Pro Leu Ser Leu Pro Val Thr Leu Gly
1           5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
            35                  40                  45

Pro Arg Arg Leu Ile Tyr Leu Val Ser Lys Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gln Thr Phe Gly Gly Gly Thr Lys Val Glu Ile Lys
            100                 105                 110

FIG. 4O hV$_H$ MAb16(a)

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
            35                  40                  45

Gly Ile Ile Asn Pro Ser Asn Gly Gly Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
            100                 105                 110

Val Thr Val Ser Ser
        115

FIG. 4P hV$_L$ MAb16(a)

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Tyr Trp Phe Gln Gln Arg Pro Gly Gln Ser
            35                  40                  45

Pro Arg Arg Leu Ile Tyr Leu Val Ser Asn Arg Asp Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
            85                  90                  95

Thr His Ser Pro Tyr Thr Phe Gly Gln Gly Thr Lys Leu Glu Ile Lys
            100                 105                 110
```

FIG. 4Q hV$_H$ MAb16(b)

Gln Val Gln Leu Val Gln Ser Gly Ala Glu Val Lys Lys Pro Gly Ala
1         5                    10                   15

Ser Val Lys Val Ser Cys Lys Ala Ser Gly Tyr Thr Phe Thr Ser Tyr
              20                  25                   30

Tyr Met His Trp Val Arg Gln Ala Pro Gly Gln Gly Leu Glu Trp Met
          35                   40                   45

Gly Ile Ile Asn Pro Ser Asn Gly Gly Thr Ser Tyr Ala Gln Lys Phe
      50                   55                   60

Gln Gly Arg Val Thr Met Thr Arg Asp Thr Ser Thr Ser Thr Val Tyr
65                   70                   75                   80

Met Glu Leu Ser Ser Leu Arg Ser Glu Asp Thr Ala Val Tyr Tyr Cys
                  85                   90                   95

Thr Arg Gly Gly Tyr Tyr Pro Phe Asp Tyr Trp Gly Gln Gly Thr Thr
                  100                  105                  110

Val Thr Val Ser Ser
          115

FIG. 4R hV$_L$ MAb16(b)

Asp Val Val Met Thr Gln Ser Pro Leu Ser Leu Pro Val Thr Leu Gly
1           5                   10                  15

Gln Pro Ala Ser Ile Ser Cys Arg Ser Ser Gln Ser Leu Leu Asp Ser
            20                  25              30

Asp Gly Lys Thr Tyr Leu Asn Trp Phe Gln Gln Arg Pro Gly Gln Ser
            35                  40                  45

Pro Arg Arg Leu Ile Tyr Leu Val Ser Asn Arg Asp Ser Gly Val Pro
            50              55              60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Trp Gln Gly
            85                  90                  95

Thr His Ser Pro Tyr Thr Phe Gly Gln Gly Thr Lys Leu Glu Ile Lys
            100                 105                 110

FIG. 4S hV$_H$ MAb16(c)

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
                35                  40                  45

Gly Glu Ile Asn Pro Ser Asn Gly Gly Thr Asn Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
                100                 105                 110

Val Thr Val Ser Ser
            115

FIG. 4T hV$_L$ MAb16(c)

Asp Val Val Met Thr Gln Ser Pro Leu Ser Leu Pro Val Thr Leu Gly
1           5                   10                  15

Gln Pro Ala Ser Ile Ser Cys Arg Ser Ser Gln Ser Leu Leu Asp Ser
            20                  25                  30

Asp Gly Lys Thr Tyr Leu Tyr Trp Phe Gln Gln Arg Pro Gly Gln Ser
            35                  40                  45

Pro Arg Arg Leu Ile Tyr Leu Val Ser Glu Arg Asp Ser Gly Val Pro
        50              55                  60

Asp Arg Phe Ser Gly Ser Gly Ser Gly Thr Asp Phe Thr Leu Lys Ile
65              70                  75                      80

Ser Arg Val Glu Ala Glu Asp Val Gly Val Tyr Tyr Cys Trp Gln Gly
            85                  90                      95

Thr His Ser Pro Tyr Thr Phe Gly Gln Gly Thr Lys Leu Glu Ile Lys
                100                 105                 110

FIG. 4U hV$_H$ MAb19(a)

Gln Val Gln Leu Gln Glu Ser Gly Pro Gly Leu Val Lys Pro Ser Gln
1              5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Ile Ser Phe Ser Gly Tyr Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Glu Val Asn Tyr Gly Asp Ser Tyr His Phe Asp Tyr Trp Gly
        100                 105                 110

Gln Gly Thr Leu Val Thr Val Ser Ser
        115                 120

FIG. 4V hV$_L$ MAb19(a)

```
Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
            20                  25                  30

Ile Glu Trp His Gln Gln Pro Glu Lys Gly Pro Arg Tyr Leu Met
            35                  40                  45

Lys Val Lys Lys Asp Gly Ser His Ser Lys Gly Asp Gly Ile Pro Asp
    50                  55                  60

Arg Phe Ser Gly Ser Ser Ser Gly Ala Glu Arg Tyr Leu Thr Ile Ser
65              70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
            100                 105                 110

Glu Ile Lys
        115
```

FIG. 4W hV$_H$ MAb19(b)

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20              25                  30

Tyr Ala Trp Ser Trp Ile Arg Gln His Pro Gly Lys Gly Leu Glu Trp
        35              40              45

Ile Gly Tyr Ile Ser Phe Ser Gly Tyr Thr Tyr Tyr Asn Pro Ser Leu
        50              55              60

Lys Ser Arg Val Thr Ile Ser Val Asp Thr Ser Lys Asn Gln Phe Ser
65              70              75              80

Leu Lys Leu Ser Ser Val Thr Ala Ala Asp Thr Ala Val Tyr Tyr Cys
                85              90              95

Ala Arg Glu Val Asn Tyr Gly Asp Ser Tyr His Phe Asp Tyr Trp Gly
            100             105             110

Gln Gly Thr Leu Val Thr Val Ser Ser
        115             120

FIG. 4X hV$_L$ MAb19(b)

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
                20              25                  30

Ile Ala Trp His Gln Gln Pro Glu Lys Gly Pro Arg Tyr Leu Met
            35              40                  45

Lys Val Lys Lys Asp Gly Ser His Ser Lys Gly Asp Gly Ile Pro Asp
    50                  55                  60

Arg Phe Ser Gly Ser Ser Ser Gly Ala Glu Arg Tyr Leu Thr Ile Ser
65              70                  75                      80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
            100                 105                 110

Glu Ile Lys
    115

FIG. 4Y hV$_H$ MAb19(c)

Gln Val Gln Leu Gln Glu Ser Gly Pro Gly Leu Val Lys Pro Ser Gln
1              5                       10                      15

Thr Leu Ser Leu Thr Cys Thr Val Ser Gly Tyr Ser Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Ile Ser Phe Ser Gly Tyr Thr Ser Tyr Asn Pro Ser Leu
        50              55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Glu Val Asn Tyr Gly Asp Ser Tyr His Phe Asp Tyr Trp Gly
        100                 105                 110

Gln Gly Thr Leu Val Thr Val Ser Ser
        115                 120

FIG. 4Z hV$_L$ MAb19(c)

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
                20              25                  30

Ile Glu Trp His Gln Gln Pro Glu Lys Gly Pro Arg Tyr Leu Met
        35                  40                  45

Glu Val Lys Lys Asp Gly Ser His Ser Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
                100                 105                 110

Glu Ile Lys
        115

US 8,900,817 B2

PROGASTRIN AND LIVER PATHOLOGIES

1. CROSS REFERENCE TO RELATED APPLICATIONS

This application claims the benefit under 35 U.S.C. §119(e) of U.S. Provisional Application No. 61/293,557, filed Jan. 8, 2010, the content of which is incorporated by reference in its entirety.

2. REFERENCE TO SEQUENCE LISTING

The Sequence Listing submitted concurrently herewith under 37 CFR §1.821 in a computer readable form (CRF) via EFS-Web as file name "BR003SEQLIST.txt" is incorporated herein by reference. The electronic copy of the Sequence Listing was created on Dec. 28, 2010, with a file size of 77.9 Kbytes.

3. BACKGROUND

The present disclosure provides methods and materials for the diagnosis and screening of liver pathologies, including proliferative or degenerative diseases of the liver; and more particularly, methods and materials for the quantification or determination of progastrin levels to diagnose liver pathologies.

3.1. Background of the Gastrin and Progastrin Hormones

Gastrin is a gut peptide hormone that functions as a stimulant of gastric acid secretion. In the adult mammal, it is produced principally by the G cells of the gastric antrum and to a variable extent in the upper small intestine and pancreas, with barely detectable amounts in the colon. Recently, there has been increasing interest in the role of the gastrin family of peptides in colorectal carcinogenesis. In particular, there is evidence that the precursor forms of gastrin (progastrin and glycine-extended gastrin), which were previously thought to be inactive, play a role in the development of colorectal cancer.

The gastrin gene is translated into a 101-amino acid polypeptide, called preprogastrin, which contains a signal sequence (underlined) that is cleaved, giving rise to progastrin, an 80-amino acid polypeptide. In turn, progastrin is processed to provide the cleavage product $G_{34}$, a 34-amino acid peptide corresponding to residues 38 to 71 of progastrin. $G_{34}$ is then extended at its carboxy terminus with a glycine residue, generating glycine-extended $G_{34}$ ($G_{34}$-Gly). A by-product of progastrin cleavage is a 6-amino acid peptide, called the C-terminal flanking peptide, or CTFP, which corresponds in sequence to residues 75 to 80 of progastrin. $G_{34}$-Gly is then further cleaved to generate a 18-residue polypeptide corresponding in sequence to residues 55 to 72 of progastrin and referred to as $G_{17}$-Gly. Removal of the C-terminal glycines of $G_{34}$-Gly and $G_{17}$-Gly, followed by C-terminal amidation, yields $G_{34}$ and $G_{17}$, respectively, both of which are C-terminally amidated.

Most assays for progastrin do not distinguish between progastrin and other gastrin gene products, resulting in an inaccurate measurement of full-length progastrin levels. Because progastrin levels play a role in one or more diseases, accurate means for the measurement of progastrin are desirable.

3.2. Background of Liver Pathologies

Many liver pathologies are difficult to diagnose. For example, liver cancer cannot be diagnosed by routine blood tests. Physician screening with the tumor marker alpha-feto-protein (AFP) is usually necessary. However, elevated AFP levels are not specific for liver cancer. In adults, high blood levels (over 500 ng/mL) of AFP are seen in three situations: liver cancer, germ cell tumors (cancers of the testes and ovaries), and metastatic cancer of the liver (a cancer originating in other organs). In addition, the sensitivity of AFP for liver cancer is about 60%. In other words, an elevated AFP blood level is seen in only about 60% of liver cancer patients; 40% of patients with liver cancer have normal AFP levels. Another difficult to diagnose liver pathology is cirrhosis, a consequence of chronic liver disease characterized by scarring of the liver and poor liver function. The gold standard of diagnosis is by way of liver biopsy, an invasive technique.

Hepatitis C is an infectious disease affecting the liver, caused by the hepatitis C virus (HCV). The infection is often asymptomatic, but once established, chronic infection can progress to scarring of the liver (fibrosis) and advanced scarring (cirrhosis). Hepatitis C is typically diagnosed by way of serological screening. Other means for detecting and/or confirming hepatitis C would be desirable.

Because the early and accurate detection of liver cancer, cirrhosis, and hepatitis C has the potential to increase the survival rate of a patient, there is a present and long-felt need for methods of diagnosing or detecting these pathologies, including instances where a patient has more than one or all of the aforementioned diseases.

4. SUMMARY

It has been discovered that whereas patients with one or two liver pathologies can exhibit elevated human progastrin (hPG) levels, patients with liver cancer, hepatitis C and cirrhosis exhibit extremely elevated levels of hPG that are more than merely additive of the hPG levels exhibited by patients with just one or two of these conditions. Based on the present disclosure, a patient's plasma or serum levels of hPG can be used to assign a risk factor for liver pathology. Moreover, excessive serum or plasma levels of hPG can be used to diagnose a patient suffering from a liver cancer, hepatitis C and cirrhosis.

Liver cancers that can be diagnosed by the methods of the disclosure include primary liver cancers (e.g., hepatocellular carcinoma, a cancer originating in the liver) and secondary liver cancers.

Methods of diagnosis are also provided wherein a patient is identified as suffering from a hepatic or liver condition if a human progastrin (hPG) level above a threshold value (for example, at least about 400, 450, 500, 550, 600, 650, 700, or 750 pM) is detected. Such methods can also be useful as a standard diagnostic in populations having a higher than average incidence of a liver disease, for example, in drug or alcohol-user populations or persons residing in geographic regions with higher than average incidences of liver disease. Accordingly, methods of detecting elevated hPG levels in such populations are also provided.

The present disclosure also provides methods for assigning a patient to a risk group for one or more liver pathologies such as liver cancer (e.g., hepatocellular carcinoma), hepatitis C and cirrhosis based on the patient's hPG levels. For example, a first threshold level of hPG can indicate that the patient is at a "low risk" for liver pathology; a second threshold level of hPG can indicate that the patient is at an "elevated risk" for liver pathology; a third threshold level of hPG can indicate that the patient is at a "high risk" for liver pathology; and a fourth threshold level of hPG can indicate that the patient is at a "severe risk" for liver pathology.

Quantified hPG levels can also be used with additional biomarkers, such as alpha-fetoprotein ("AFP") to aid in the identification, diagnosis, differentiation of, or risk assignment for, liver pathologies.

The methods disclosed herein can be used to determine appropriate therapeutic courses of action. In some instances, it is useful to screen patients who are already diagnosed with a liver pathology to determine if further treatment options are warranted. Accordingly, in certain aspects, a patient who has been previously diagnosed with a liver pathology is diagnosed as suffering from a further hepatic or liver condition on the basis of hPG levels in the patient's biological sample. The previous liver pathology can be hepatitis C, cirrhosis, or liver cancer, such as hepatocellular carcinoma. Advantageously, extremely high levels of hPG (e.g., hPG concentrations of above 400, 450, 500, 550, 600, 650, 700 pM) indicate the patient has all of these conditions.

A patient whose hPG levels indicate that the patient has a liver pathology, or a patient previously diagnosed with a liver condition and whose hPG levels are indicative of greater than one liver condition, can be subjected to further testing to identify specific liver conditions. The patient can be tested for liver cancer, hepatitis C, or cirrhosis of the liver.

Patients who have been identified as having one or more liver pathologies using methods of the disclosure can be treated for their condition. Patients undergoing treatment for a hepatic pathology can also have their hPG levels monitored to evaluate disease progression and/or treatment efficacy. A patient whose hPG levels remain above a threshold value may continue to receive treatment.

In the practice of the methods disclosed herein, the particular assay for measuring hPG levels is not critical provided the measured hPG level is accurate. In some embodiments, anti-hPG antibodies are conveniently used to measure hPG levels. As noted, hPG is cleaved by the body into smaller peptides. It is preferred that hPG be detected and measured in the methods of the disclosure using assays that do not detect byproducts of progastrin processing so to avoid inaccurate hPG measurements. This can be achieved by the use of antibodies that bind to full length hPG but not to smaller hPG peptides. This can also be achieved by the use of two different antibodies that both bind to full length hPG but to the extent that the antibodies bind to smaller hPG peptides, do not both bind to the same smaller hPG peptides. In such assays, the only product bound by both antibodies is full length hPG. For example, antibodies that bind to the C- and N-terminal epitopes of hPG allow detection and measurement of full length hPG without detection and measurement of smaller hPG peptides. Thus, in certain aspects, the disclosure provides a method of diagnosing a patient wherein a biological sample is contacted with a first antibody that binds to a first epitope of hPG, preferably a C- or N-terminal epitope, and a second antibody that binds to for a different epitope of hPG, preferably an epitope at the other terminus In an exemplary method that utilizes an anti-hPG antibody for detection and measurement of hPG, a patient is identified as suffering from a hepatic or liver condition by contacting a sample from the patient with at least one anti-hPG antibody; and determining whether the sample has a hPG concentration above a threshold value, for example, at least about 400, 450, 500, 550, or 600 pM, often 400, 450, or 500 pM, based on the amount of hPG bound to the antibody.

The methods of the disclosure generally include assaying a biological sample for hPG levels. The biological sample can be plasma or serum. Tissue levels can also be used; however, levels of hPG measured in tissue are expected to differ from levels of hPG found in serum or plasma but will be elevated relative to a patient's normal hPG level when a patient is suffering from liver pathologies. Thus, tissue levels of hPG can also be used to monitor a patient's risk or status of liver pathology. When a tissue sample is used, progastrin can be detected using an immunoassay performed on a cell or tissue extract, or can utilize immunohistochemical techniques employing a polyclonal or monoclonal antibody labeled with a detectable marker Immunohistochemical techniques provide a qualitative measurement of progastrin levels. Suitable detectable markers include a radioactive label (such as radioactive iodine), a fluorescent label or a chemiluminescent label.

Diagnostic kits are also provided herein. A diagnostic kit can comprise, for example, one or more antibodies to progastrin optionally labeled with a detectable marker that can be used to screen, diagnose, or differentiate liver pathologies. A diagnostic kit can contain a first antibody having an affinity with the N-terminal peptide region of hPG and a second antibody having an affinity with a different epitope such as the C-terminal peptide region of hPG. The present disclosure also provides kits for carrying out methods of diagnosing liver pathologies, comprising an N-terminal anti-hPG monoclonal antibody and a monoclonal or polyclonal C-terminal anti-hPG antibody, each in a separate container, and suitable reagents. In some embodiments, one or both of the antibodies provided is or are labeled.

Methods of diagnosing whether a patient suffers from a plurality of hepatic or liver conditions are also provided, wherein a patient with a blood hPG concentration of at least about 400 pM is identified as having two or more of the following conditions: hepatitis C, liver cancer, or cirrhosis, e.g., by testing hPG levels in serum or plasma from the patient using a biochemical assay. After such a patient is identified, the patient's liver pathology can be further diagnosed using assays for hepatitis C, liver cancer, or cirrhosis. Hepatitis C can be diagnosed using a nucleic acid-based assay. Liver cancer can be diagnosed using a radiography or imaging technique (with or without contrast). Cirrhosis of the liver can be diagnosed by testing a sample from said patient for one or more serum markers of fibrosis including alpha-2-macroglobulin, haptoglobin, apolipoprotein A1, gamma-glutamyl transpeptidase (GGT), total bilirubin, and alanine transaminase (ALT). The patient may have other diagnostically important markers, such as elevated serum alpha-fetoprotein and/or des-gamma carboxyprothrombin, and the method of diagnosis or treatment can further comprise a step of measuring such levels.

Following diagnosis, a patient can be treated for his or her liver condition using conventional agents, for example, a patient with hepatitis C can be treated with pegylated interferon-alpha-2a, pegylated interferon-alpha-2b, and/or viral drug ribavirin; a patient with cirrhosis can be treated with liver transplant surgery and symptomatic treatment for complications of cirrhosis; and a patient diagnosed with liver cancer can be treated with radiotherapy and/or chemotherapy.

Patients can also be monitored using the techniques of the disclosure. In one method, the disease status of a patient with a hepatic or liver disease is monitored by subjecting a patient suffering from a hepatic or liver disease and having a blood hPG concentration above a threshold amount a therapeutic regimen for said hepatic or liver disease. After treatment, it is determined whether said patient continues to have a blood hPG concentration above the threshold amount and if so, continuing the therapeutic regimen. If the patient no longer has a blood hPG concentration above the threshold amount, the patient's hPG levels can be periodically monitored to determine whether they rise above said threshold amount, allowing treatment to be reinitiated.

Systems for diagnosing a patient's liver or hepatic health status are also provided. Systems of the disclosure comprise one or more of the following components: an input that receives values of a patient's blood hPG concentration, a processor configured to compare the patient's blood hPG concentration to a reference blood hPG concentration, the processor configured to output a risk level for liver pathology for the patient based wholly or in part on the patient's blood hPG concentration, and a display configured to display the risk level for liver pathology. The systems can be adapted so that the processor outputs low, elevated, high or severe risk level determinations for a liver pathology. The system can also comprise an input to receive values for a patient's alpha-fetoprotein (AFP) levels, wherein the processor is configured to compare the AFP level to a reference AFP level and to output a risk level for a liver pathology based on the hPG and AFP levels. Threshold (i) hPG and (ii) hPG and AFP levels for different risk groups are disclosed herein.

A computer readable storage medium is also provided that has stored therein data representing instructions executable by a programmed processor for use in diagnosing patient's liver or hepatic health status, the storage medium comprising instructions for comparing a patient's blood hPG concentration to a reference blood hPG concentration; and outputting a risk level for liver pathology for the patient based wholly or in part on the patient's blood hPG concentration. The medium can output risk levels, e.g., low, elevated, high or severe risk level determinations for a liver pathology. The medium can also comprise data for comparing a patient's blood AFP level to a reference level for outputting risk level determinations. Threshold (i) hPG and (ii) hPG and AFP levels for different risk groups are disclosed herein.

5. BRIEF DESCRIPTION OF THE FIGURES

FIG. 1 provides amino acid sequences of pre-progastrin (where the signal peptide is underlined), progastrin and products of progastrin processing, including $G_{34}$, $G_{34}$-Gly, $G_{17}$, $G_{17}$-Gly, and the C-terminal flanking peptide, CTFP.

FIG. 2 provides a bar chart of hPG values indicative of certain liver pathologies.

FIG. 3A-3L provide polypeptide, and corresponding polynucleotide, sequences of VH and VL chains for exemplary murine anti-hPG monoclonal antibodies.

FIG. 3A shows the polynucleotide (SEQ ID NO:16) and polypeptide (SEQ ID NO:12) murine VH chain for anti-hPG MAb3 and FIG. 3B shows the polynucleotide (SEQ ID NO:17) and polypeptide (SEQ ID NO:13) murine VL chain for anti-hPG MAb3.

FIG. 3C shows the polynucleotide (SEQ ID NO:18) and polypeptide (SEQ ID NO:14) murine VH chain for anti-hPG MAb4 and FIG. 3D shows the polynucleotide (SEQ ID NO:19) and polypeptide (SEQ ID NO:15) murine VL chain for anti-hPG MAb4.

FIG. 3E shows the polynucleotide (SEQ ID NO:67) and polypeptide (SEQ ID NO:59) murine VH chain for anti-hPG MAb8 and FIG. 3F shows the polynucleotide (SEQ ID NO:71) and polypeptide (SEQ ID NO:63) murine VL chain for anti-hPG MAb8.

FIG. 3G shows the polynucleotide (SEQ ID NO:68) and polypeptide (SEQ ID NO:60) murine VH chain for anti-hPG MAb13 and FIG. 3H shows the polynucleotide (SEQ ID NO:72) and polypeptide (SEQ ID NO:74) murine VL chain for anti-hPG MAb13.

FIG. 3I shows the polynucleotide (SEQ ID NO:69) and polypeptide (SEQ ID NO:61) murine VH chain for anti-hPG MAb16 and FIG. 3J shows the polynucleotide (SEQ ID NO:73) and polypeptide (SEQ ID NO:65) murine VL chain for anti-hPG MAb16.

FIG. 3K shows the polynucleotide (SEQ ID NO:70) and polypeptide (SEQ ID NO:62) murine VH chain for anti-hPG MAb19 and FIG. 3L shows the polynucleotide (SEQ ID NO:74) and polypeptide (SEQ ID NO:66) murine VL chain for anti-hPG MAb19.

Figure 2:
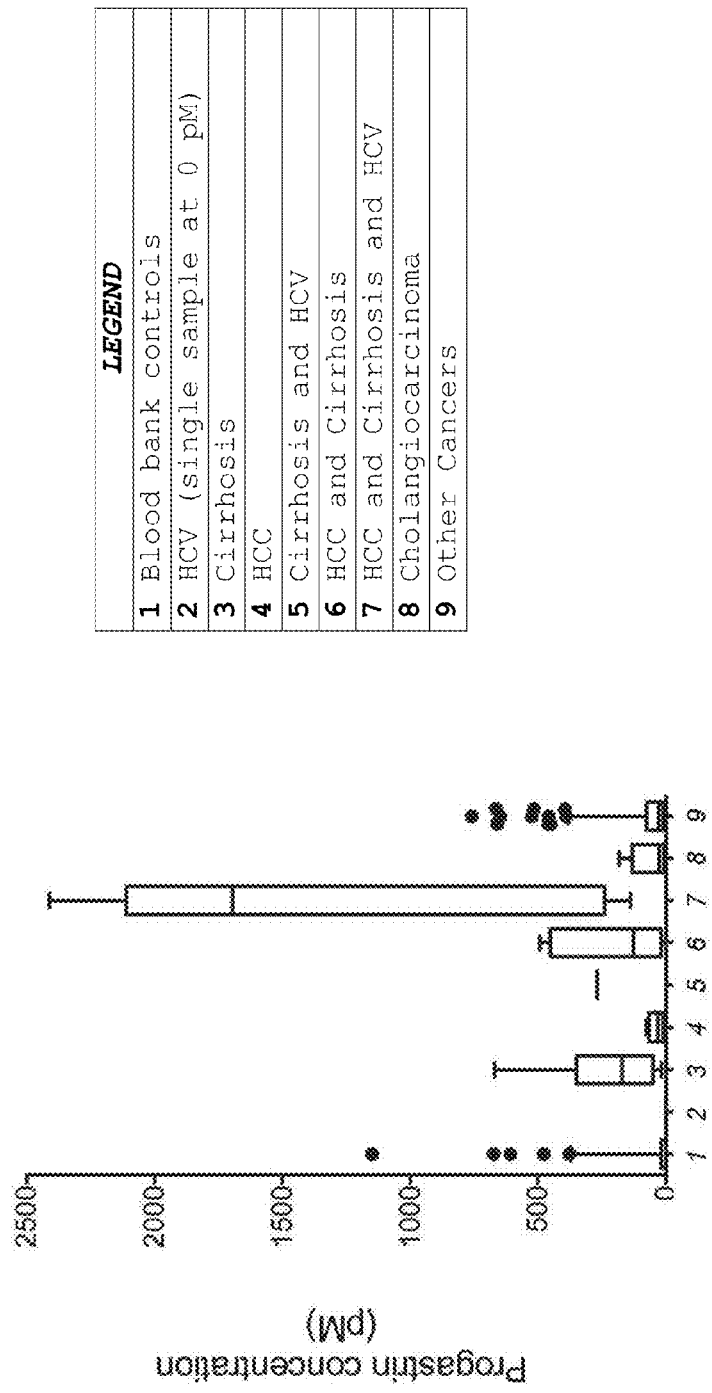

FIG. 4A-4Z provide the polypeptide sequences of VH and VL chains for exemplary human anti-hPG monoclonal antibodies.

FIG. 4A shows the polypeptide (SEQ ID NO:21) human VH chain for anti-hPG MAb3 and FIG. 4B shows the polypeptide (SEQ ID NO:22) human VL chain for anti-hPG MAb3.

FIG. 4C shows the polypeptide (SEQ ID NO:23) human VH chain for anti-hPG MAb4 and FIG. 4D shows the polypeptide (SEQ ID NO:24) human VL chain for anti-hPG MAb4.

FIG. 4E shows the polypeptide (SEQ ID NO:75) human VH chain for anti-hPG MAb8(a) and FIG. 4F shows the polypeptide (SEQ ID NO:76) human VL chain for anti-hPG MAb8(a).

FIG. 4G shows the polypeptide (SEQ ID NO:77) human VH chain for anti-hPG MAb8(b) and FIG. 4H shows the polypeptide (SEQ ID NO:78) human VL chain for anti-hPG MAb8(b).

FIG. 4I shows the polypeptide (SEQ ID NO:79) human VH chain for anti-hPG MAb8(c) and FIG. 4J shows the polypeptide (SEQ ID NO:76) human VL chain for anti-hPG MAb8(c).

FIG. 4K shows the polypeptide (SEQ ID NO:80) human VH chain for anti-hPG MAb13(a) and FIG. 4L shows the polypeptide (SEQ ID NO:81) human VL chain for anti-hPG MAb13 (a).

FIG. 4M shows the polypeptide (SEQ ID NO:82) human VH chain for anti-hPG MAb13(b) and FIG. 4N shows the polypeptide (SEQ ID NO:83) human VL chain for anti-hPG MAb13(b).

FIG. 4O shows the polypeptide (SEQ ID NO:84) human VH chain for anti-hPG MAb16(a) and FIG. 4P shows the polypeptide (SEQ ID NO:85) human VL chain for anti-hPG MAb16(a).

FIG. 4Q shows the polypeptide (SEQ ID NO:86) human VH chain for anti-hPG MAb16(b) and FIG. 4R shows the polypeptide (SEQ ID NO:87) human VL chain for anti-hPG MAb16(b).

FIG. 4S shows the polypeptide (SEQ ID NO:88) human VH chain for anti-hPG MAb16(c) and FIG. 4T shows the polypeptide (SEQ ID NO:89) human VL chain for anti-hPG MAb16(c).

FIG. 4U shows the polypeptide (SEQ ID NO:90) human VH chain for anti-hPG MAb19(a) and FIG. 4V shows the polypeptide (SEQ ID NO:91) human VL chain for anti-hPG MAb19(a).

FIG. 4W shows the polypeptide (SEQ ID NO:92) human VH chain for anti-hPG MAb19(b) and FIG. 4X shows the polypeptide (SEQ ID NO:93) human VL chain for anti-hPG MAb19(b).

FIG. 4Y shows the polypeptide (SEQ ID NO:94) human VH chain for anti-hPG MAb19(c) and FIG. 4Z shows the polypeptide (SEQ ID NO:95) human VL chain for anti-hPG MAb19(c).

6. DETAILED DESCRIPTION

6.1. Definitions

Unless indicated otherwise, the following terms are intended to have their ordinary meanings, which are discussed below in the context of the present disclosure:

"Human Progastrin" or "hPG" is a polypeptide of the amino acid sequence identified as SEQ ID NO:20. As used herein, hPG is defined as comprising the primary protein product of the gastrin gene; i.e., preprogastrin without the signal- or pre-peptide. See Rehfeld et al. (2004) *Regulatory Peptides* 120(1-3):177-183. hPG consists of three well defined regions divided by two d-Arg cleavage sites. Accordingly, unless otherwise defined, hPG consists of the products of preprogastrin processing which retain the two d-Arg sites. hPG does not include the "gastrins," i.e., $G_{34}$ and $G_{17}$ but can comprise, for example, short truncates (up to 1, 2, 3, 4 or 5 amino acids) or variants of hPG which retain the two d-Arg sites located at or about amino acids 36/37 and 73/74. See FIG. 1.

"Biological marker" or "biomarker" means a characteristic that is objectively measured and evaluated as an indicator of normal biologic processes, pathogenic processes, or pharmacologic responses to a therapeutic intervention.

A "sandwich assay" refers to a specific type of immunoassay that can be used to quantify the amount of a compound that interacts with a sample. The sandwich assay is so-called because the antigen of the sample is bound between a capture antibody and a detecting or reference antibody. In the sandwich assays of the disclosure, human progastrin is bound between anti-hPG antibodies. The assay provides a quantification of hPG but not precursors or products thereof, thereby providing a more accurate measure of hPG concentration. Advantageously, the antibodies of the disclosure directed against the N-terminal or C-terminal regions of progastrin are also specific for progastrin separately. Smaller processing fragments of progastrin are therefore less likely to act as competitors to one or the other antibody thereby possibly biasing assay results.

A "subject" or "patient" is used interchangeably herein, which refers to a vertebrate, preferably a mammal, more preferably a human.

An "antibody" or "Ab" refers to an immunoglobulin molecule that specifically binds to, or is immunologically reactive with, a particular antigen, and includes polyclonal, monoclonal, genetically engineered and otherwise modified forms of antibodies, including but not limited to chimeric antibodies, humanized antibodies, and antigen binding fragments of antibodies, including, e.g., Fab', F(ab')$_2$, Fab, Fv, rIgG, and scFv fragments. In various embodiments, anti-hPG monoclonal antibodies comprise all or a portion of a constant region of an antibody. In some embodiments, the constant region is an isotype selected from: IgA (e.g., IgA$_1$ or IgA$_2$), IgD, IgE, IgG (e.g., IgG$_1$, IgG$_2$, IgG$_3$ or IgG$_4$), and IgM. Antibodies (including monoclonal antibodies) can be generated from any of several species including but not limited to mouse, rabbit, rat, pig, guinea pig, chicken, donkey, horse, camel, and lama.

As used herein, an antibody is "highly specific for" hPG if it binds to full-length progastrin but does not bind at all to CTFP, to amidated gastrin, or to glycine-extended gastrin, and "specific for hPG" or an "antibody specifically binds to hPG" if it exhibits at least about 5-fold greater binding to hPG than to CTFP and the other products of the gastrin gene, as measured in standard binding assays. An ELISA assay that can used to assess the specificity of a particular anti-hPG antibody is provided in Example 4.

Such specific anti-hPG antibodies (referred to herein as "anti-hPG antibodies") may be polyclonal ("anti-hPG PAbs") or monoclonal ("anti-hPG MAbs"), although for therapeutic uses and, in some instances, diagnostic or other in vitro uses, monoclonal antibodies are preferred.

The term "monoclonal antibody" as used herein is not limited to antibodies produced through hybridoma technology. A monoclonal antibody is derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof In many uses of the present disclosure, including in vivo use of the anti-hPG monoclonal antibodies in humans and in vitro detection assays, chimeric, primatized, humanized, or human antibodies can suitably be used.

The term "scFv" refers to a single chain Fv antibody in which the variable domains of the heavy chain and the light chain from a traditional antibody have been joined to form one chain.

References to "VH" refer to the variable region of an immunoglobulin heavy chain of an antibody, including the heavy chain of an Fv, scFv, or Fab. References to "VL" refer to the variable region of an immunoglobulin light chain, including the light chain of an Fv, scFv, dsFv or Fab. Antibodies (Abs) and immunoglobulins (Igs) are glycoproteins having the same structural characteristics. While antibodies exhibit binding specificity to a specific target, immunoglobulins include both antibodies and other antibody-like molecules that lack target specificity. Native antibodies and immunoglobulins are usually heterotetrameric glycoproteins of about 150,000 Daltons, composed of two identical light (L) chains and two identical heavy (H) chains. Each heavy chain has at one end a variable domain (VH) followed by a number of constant domains. Each light chain has a variable domain at one end (VL) and a constant domain at its other end.

Anti-hPG monoclonal antibodies of the disclosure comprise "complementarity-determining regions (CDRs)." CDRs are also known as hypervariable regions both in the light chain and the heavy chain variable domains. The more highly conserved portions of variable domains are called the framework (FR). As is known in the art, the amino acid position/boundary delineating a hypervariable region of an antibody can vary, depending on the context and the various definitions known in the art. Some positions within a variable domain can be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The disclosure provides antibodies comprising modifications in these hybrid hypervariable positions. The variable domains of native heavy and light chains each comprise four FR regions, largely by adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the target-binding site of antibodies (See Kabat et al., *Sequences of Proteins of Immunological Interest*, National Institute of Health, Bethesda, Md. 1987).

The term "epitope" refers to any portion (determinant) of a protein that is capable of eliciting an immune response and being specifically bound by an antibody. Epitope determinants usually consist of active surface groupings of molecules such as amino acids or GAG side chains and usually have specific three-dimensional structural characteristics, as well as specific charge characteristics. Two antibodies are said to bind to substantially the same epitope of a protein (or the overlapping epitope of a protein) if amino acid mutations in the protein that reduce or eliminate binding of one antibody also reduce or eliminate binding of the other antibody, and/or if the antibodies compete for binding to the protein, i.e., binding of one antibody to the protein reduces or eliminates binding of the other antibody. The determination of whether two antibodies bind substantially to the same epitope is accomplished by the methods known in the art, such as a competition assay. In conducting an antibody competition study between a control antibody (for example, one of the anti-progastrin antibodies described herein) and any test antibody, one can first label the control antibody with a detectable label, such as, biotin, enzymatic, radioactive label, or fluorescent label to enable the subsequent identification. A test (unlabeled) antibody that binds to substantially the same epitope as the control (labeled) antibody should be able to block control antibody binding and thus should reduce control antibody binding.

An "assay specific for hPG" or an "assay specific for human progastrin" refers to an assay that distinguishes full length hPG from CTFP and the other products of the gastrin gene. In the context of an antibody-based diagnostic assay, an assay specific for hPG can utilize an antibody that specifically binds to hPG. Alternatively, an assay specific for hPG can utilize two antibodies that both bind to full length hPG but otherwise do not both bind to the same gastrin gene products, such that hPG is the only molecule produced by the gastrin gene that is recognized by both antibodies. For example, antibodies that bind to C- and N-terminal epitopes of hPG can be used in an assay that distinguishes hPG from other gastrin gene peptides.

With respect to the use of the term cancer, it is noted that in patients in whom cells from the primary (original) tumor have broken free and migrated to another location within the body, typically through the lymph or blood, via a process called "metastasis," to form another, metastatic (or secondary) tumor, the secondary or metastatic tumor is typically of the same type as the original tumor, regardless of its new location, such that the disease is referred to as metastatic cancer, and not cancer of the new resident tissue. For example, pancreatic cancer that has spread to the liver is metastatic pancreatic cancer, not liver cancer. Accordingly, metastatic hepatocellular carcinoma refers to a cancer originating in the liver and metastasizing elsewhere. Secondary liver cancer (i.e., metastatic cancer from a non-liver source that has metastasized to the liver) can also be diagnosed based on excessive levels of hPG. For example, a colorectal cancer that has metastasized (i.e. metastatic colorectal cancer) to the liver is a form of secondary liver cancer. In other words, cancer of the liver is detectable using hPG levels in serum, plasma, or tissue in both primary and secondary liver cancers.

6.2. Progastrin Levels and Liver Pathologies

Normal progastrin levels are generally considered to be less than 20 to 50 pM, typically between 0 and 5 pM. The present disclosure demonstrates that patients with one or two liver pathologies can exhibit elevated human progastrin (hPG) levels, and that patients with liver cancer, hepatitis C and cirrhosis exhibit extremely elevated levels of hPG.

FIG. 2 graphically illustrates hPG levels in patients with one or more liver pathologies as determined by an ELISA-sandwich assay using anti-hPG antibodies. Outer bounds of boxed areas indicate the 25th to 75th percentile. Whiskers indicate the 5th to 95th percentile. Single lines represent the median. Dots indicate outliers. The following Table summarizes 5th to 95th percentile data:

TABLE 1

| Progastrin Levels (pM) in Patients with Liver Pathologies (5-95 Percentile) | |
|---|---|
| Liver Cancer | Cirrhosis |
| 0 to 100 (20)† | 10 to 700 (90) |
| Liver Cancer and Hepatitis C | Liver Cancer, Hepatitis C and Cirrhosis |
| 10 to 500 (50) | 150 to 2000 (1300-1400) |

†Values in parenthesis indicate mean hPG levels.

Based on the foregoing, hPG levels above 50 pM or 100 pM can be indicative of one or more pathologies of the liver. hPG levels of at least about 400 pM, 500 pM or 600 pM are particularly diagnostically significant as they are strongly indicative of multiple liver pathologies, particular the presence of liver cancer and cirrhosis, liver cancer and hepatitis C, and liver cancer, cirrhosis and hepatitis C.

Plasma levels for patients with only hepatitis C have been found to be similar to healthy patients in a study measuring total progastrin levels (i.e. levels of full-length progastrin and cleavage products). Konturek et al., 2003, *Scand J Gastroenterol* 6:643-647. Levels of full-length progastrin only in patients with hepatitis C are expected to be very low.

Progastrin levels can be used to assign a risk point score and a corresponding disease risk probability. For an example of a model for assigning mortality risk in patients with end-stage liver disease, see Kamath et al. (2001) *Hepatology* 33(2):464-70.

Using empirical data correlating determined progastrin levels with liver disease states, a point score and associated disease risk probability can be derived from the levels of biomarkers, such as progastrin and optionally other biomarkers. The disease risk probability can be qualitatively described using four risk groups: low risk, elevated risk, higher risk, and severe risk.

The risk levels referred to in the present disclosure have the following meanings:
"Low Risk" means the patient's levels of biological marker(s) do not indicate the presence of a given liver pathology.
"Elevated Risk" means the patient's levels of biological marker(s) indicate an increased risk of a given liver pathology. The risk is of such magnitude that further testing is warranted.
"High Risk" means the patient's levels of biological marker(s) indicate a greatly increased risk of a given liver pathology. The risk is of such magnitude that further testing is required. A tentative diagnosis based on the specificity of the biological markers might be justified.
"Severe Risk" means the patient's levels of biological marker(s) are clearly abnormal and indicate an underlying pathology. A diagnosis, subject to the specificity of the biological marker(s), can be made.

Patients who have serum or plasma progastrin levels below 0 pM to 100 pM have a low risk for a diagnosis of both liver cancer, e.g., hepatocellular carcinoma and cirrhosis, and an extremely low risk for a diagnosis of all three of liver cancer, cirrhosis and hepatitis C. Patients with normal serum or plasma levels of progastrin (e.g., 0 to 5 pM) or slightly elevated levels (up to 100 pM) can nonetheless have liver cancer. Accordingly, it is advisable to further test a patient with serum or plasma levels of hPG of 100 pM or lower to evaluate whether he or she has liver cancer.

Patients who have serum or plasma progastrin levels of between 100 pM and 400 pM are unlikely to have liver cancer without other hepatic pathologies. Such patients have a high risk of having cirrhosis (with or without liver cancer) and an elevated risk of having hepatitis C in addition. Patients who have serum or plasma progastrin levels above 400 pM are at a severe risk of having liver cancer, hepatitis C and cirrhosis.

The relationship between a patient's hPG levels and liver pathology status can be used in a variety of diagnostic methods. The diagnostic methods generally entail comparing hPG levels in a patient's sample to a normal value of hPG, for example the hPG levels from a healthy individual or a pool of healthy individual. If hPG levels are elevated, the elevated level is correlated with a likely liver pathology, for example on the basis of the risk assignments provided above. Such methods optionally include a step in which a patient provides a sample of a body fluid. The body fluid can then by analyzed for levels of hPG, preferably by a biochemical assay.

In certain applications, testing a patient's level of a cancer marker in conjunction with the patient's level of hPG can be used to increase the specificity of a liver cancer marker in a patient, or to assign a risk point score and a corresponding disease risk probability. A preferred secondary marker is alpha-fetoprotein (AFP). Serum AFP, a fetal-specific glycoprotein antigen, is the most widely used tumor marker for detecting patients with liver cancer, e.g., hepatocellular carcinoma. The reported sensitivity of AFP for detecting hepatocellular carcinoma varies widely in both hepatitis B virus (HBV)-positive and HBV-negative populations, which is attributable to overlap between screening and diagnosis study designs. When AFP is used for screening of high-risk populations, a sensitivity of 39% to 97%, specificity of 76% to 95%, and a positive predictive value (PPV) of 9% to 32% have been reported. AFP is not specific for liver cancer. Titers also rise in acute or chronic hepatitis, in pregnancy, and in the presence of germ cell tumors.

The following Table indicates relative risk for a given liver pathology based on hPG levels in conjunction with AFP levels. Assignment of relative risk on the basis of both hPG and AFP levels provides a more sensitive and accurate test for liver pathologies than on the basis of AFP alone.

TABLE 2

Relative Risk for Liver Pathologies at Determined Progastrin and AFP Levels

| | | Progastrin Level | | |
|---|---|---|---|---|
| | | 0-100 pM | 100-400 pM | >400 pM |
| AFP Level | 0 pM to 50 pM | – | – | ++ |
| | 51 pM to 250 pM | – | + | +++ |
| | 251 pM to 500 pM | + | ++ | +++ |
| | 501 pM to 750 pM | ++ | +++ | +++ |

– = low risk,
+ = elevated risk,
++ = high risk, and
+++ = severe risk

Other secondary markers that can be used in conjunction with progastrin include oncofetal antigens, glycoprotein antigens, enzymes and isoenzymes, gene markers, and cytokines that correlate with liver cancer. Additional suitable secondary markers include glypican-3, gamma-glutamyl transferase II, alpha-1-fucosidase, transforming growth factor-betal, tumor-specific growth factor, gamma-glutamyl transferase mRNA, vascular endothelial growth factor, interleukin-8, and variants thereof Exemplary markers are described in Zhou et al. (2006) *World Journal of Gastroenterology* 12(8):1175-1181.

Liver pathologies can be confirmed by standard techniques known in the art. For example, liver cancers, such as hepatocellular carcinoma, can be confirmed by radiography or an imaging technique such as MRI, with or without biopsy and with or without quantification of a blood marker such as AFP. Hepatitis C can be confirmed by quantification of viral particles in blood, by analysis of fibrosis levels using ultrasound, using a nucleic acid-based assay and/or by fibroscan. Cirrhosis can be confirmed by diagnosis using ultrasound with or without biopsy, and/or by detecting serum markers of fibrosis. Other techniques can also be used.

6.3. Methods of Measuring Progastrin Levels

The methods of the present disclosure diagnose one or more liver pathologies and/or assign risk of liver pathology on the basis of a patient's hPG levels. Plasma and serum progastrin levels can be measured using any known analytical technique. Such techniques include, but are not limited to: ELISA, sandwich ELISA, immunoblotting (Western blotting), immunoprecipitation, BIACORE technology and the like, as well as assays based on a property of the protein including but not limited to enzymatic activity or interaction with other protein partners. For immunoassays, a preferred class of assay, one or more anti-progastrin (anti-PG) antibodies of the disclosure (whether polyclonal or monoclonal and neutralizing or non-neutralizing) can be used.

Preferred immunoassays specifically detect progastrin as opposed to other gastrin gene products, including degradation products. Sandwich assays provide such specificity for the detection of progastrin as opposed to other gastrin gene byproducts, thereby giving a more accurate measure of serum progastrin levels. Preferred immunoassay antibodies bind an antigen/epitope comprising a terminal region unique to progastrin. For example, in some embodiments, progastrin is detected using sandwich ELISA with one anti-PG antibody targeting the N-terminus of progastrin and a second anti-PG antibody targeting the C-terminus of progastrin. Exemplary antibodies are disclosed below in Section 6.4, and a general "sandwich" technique for measuring progastrin levels using anti-PG antibodies is disclosed next.

A surface, such as the wells in a 96-well plate, is prepared to which a known quantity of a first, "capture," antibody to progastrin is bound. The capture antibody can be, for example, an anti-PG antibody that binds the C- or N-terminus of progastrin. After blocking, a test sample is applied to the surface followed by an incubation period. The surface is then washed to remove unbound antigen and a solution containing a second, "detection," antibody to progastrin is applied. The detection antibody can be any of the anti-PG monoclonal antibodies described herein, provided the detection antibody binds a different epitope from the capture antibody. For example, if the capture antibody binds a C-terminal peptide region of progastrin, then a suitable detection antibody would be one that binds an N-terminal peptide region of progastrin. Progastrin levels can then be detected either directly (if, for example, the detection antibody is conjugated to a detectable label) or indirectly (through a labeled secondary antibody that binds the detection anti-PG antibody).

In a specific embodiment, human progastrin (hPG) levels are measured from a biological test sample as described in Example 1.

Receiver Operating Characteristic (ROC) curves have been generated based on plasma hPG levels as determined by a sandwich assay and demonstrate that measurement of hPG levels provides a diagnostically useful test for distinguishing between patients with one or liver pathologies and patients having other cancers and/or healthy individuals.

Exemplary antibodies for the antibody-based methods of measuring hPG levels are disclosed in the following section.

6.4. Anti-hPG Antibodies

An immunoassay for measuring hPG levels can utilize one or more polyclonal or monoclonal anti-hPG antibodies or an antigen-binding fragment thereof.

Various procedures known in the art can be used for the production of polyclonal antibodies to hPG. In a particular embodiment, rabbit polyclonal antibodies can be obtained. For the production of antibody, various host animals can be immunized by injection with hPG, including but not limited to rabbits, mice, rats, etc. Various adjuvants can be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, and dinitrophenol.

Monoclonal antibodies are preferably used in the methods of the disclosure. Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, the human B-cell hybridoma technique, and the EBV-hybridoma technique. See, e.g., Kohler and Milstein (1975) *Nature* 256:495-497; Kozbor et al. (1983) *Immunology Today* 4:72; Cole et al. (1985) pp. 77-96 in Reisfeld and Sell (1985) *Monoclonal Antibodies and Myeloma Therapy* Liss; Coligan (1991) *Current Protocols in Immunology* Lippincott; Harlow and Lane; *Antibodies: A Laboratory Manual* (1988) CSH Press; and Goding (1986) *Monoclonal Antibodies: Principles and Practice* (2d ed.) Academic Press. Such antibodies may be of any immunoglobulin class including IgG, IgM, IgE, IgA, IgD and any subclass thereof.

Recently, it has been discovered that, at least for monoclonal anti-hPG antibodies, the selection of antigen used to raise the anti-hPG antibodies may be important (see, International Application No. PCT/EP2010/006329 filed Oct. 15, 2010 and U.S. application Ser. No. 12/906,041 filed Oct. 15, 2010, the disclosures and specifically disclosed anti-hPG antibodies of which are incorporated herein by reference; hereinafter referred to as the '329 and '041 applications, respectively). As disclosed in the '329 and '041 applications, not all antigens derived from hPG stimulate production of monoclonal antibodies that specifically bind hPG under physiological conditions. Indeed, certain antigens that have been used to successfully raise polyclonal anti-hPG antibodies, such as full-length recombinant hPG (see, e.g., WO 08/076454 to Singh) and a peptide corresponding to the last ten amino acids at the C-terminal end of hPG (see WO 07/135542 to Hollande et al.) failed to generate monoclonal antibodies.

In one preferred embodiment, antibodies specific for the C- and N-terminal epitopes of hPG may be used to detect and measure hPG levels with specificity, meaning only full-length hPG is detected. As noted in the '329 and '041 applications, antigenic N-terminal and C-terminal sequences within the hPG sequence have been identified that can be used to generate monoclonal antibodies that specifically bind hPG. Interestingly, the antigenic sequence need not be limited to regions of the hPG sequence that are unique to it. Peptide antigens having regions of sequence in common with other products of the gastrin gene, for example, $G_{17}$, $G_{34}$ and CTFP, yield monoclonal antibodies that not only bind hPG, but bind it specifically.

Anti-hPG antibodies obtainable using a peptide antigen having a sequence corresponding to an N-terminal region of hPG and/or that bind an N-terminal region of hPG are referred to herein as "N-terminal anti-PG antibodies." A specific exemplary antigenic region of hPG that can be used to construct an immunogen suitable for obtaining both polyclonal and monoclonal antibodies specific for hPG corresponds to residue 1 to 14 of hPG: SWKPRSQQPDAPLG (SEQ ID NO:25). Exemplary immunogens useful for obtaining N-terminal anti-hPG antibodies, as well as CDR and VH and VL sequences of N-terminal anti-hPG monoclonal antibodies obtained with these exemplary immunogens, are provided in Table 3A, below, and the Example sections:

TABLE 3A

N-Terminal Anti-hPG Monoclonal Antibodies

| Immunogen | Hybridoma (Deposit #) | MAb | Murine CDR Sequences | | mVH and mVL Sequences | hVH and hVL Sequences (projected) |
|---|---|---|---|---|---|---|
| N1 | 43B9G11 | MAb1 | | | | |
| N1 | WE5H2G7 | MAb2 | | | | |
| N2 | 6B5B11C10 | MAb3 | VH CDR 1.3 | GYIFTSYW | (SEQ ID NO: 1) mVH.3 (SEQ ID NO. 12) | hVH.3 (SEQ ID NO: 21) |
| | | | VH CDR 2.3 | FYPGNSDS | (SEQ ID NO: 2) | |
| | | | VH CDR 3.3 | TRRDSPQY | (SEQ ID NO: 3) | |
| | | | VL CDR 1.3 | QSIVHSNGNTY | (SEQ ID NO: 4) mVL.3 (SEQ ID NO: 13) | hVL.3 (SEQ ID NO: 22) |
| | | | VL CDR 2.3 | KVS | (SEQ ID NO: 5) | |
| | | | VL CDR 3.3 | FQGSHVPFT | (SEQ ID NO: 6) | |

TABLE 3A-continued

N-Terminal Anti-hPG Monoclonal Antibodies

| Immunogen | Hybridoma (Deposit #) | MAb | Murine CDR Sequences | | mVH and mVL Sequences | | hVH and hVL Sequences (projected) | |
|---|---|---|---|---|---|---|---|---|
| N2 | 20D2C3G2 | MAb4 | VH CDR 1.4 | GYTFSSSW (SEQ ID NO: 7) | mVH.4 | (SEQ ID NO: 14) | hVH.4 | (SEQ ID NO: 23) |
| | | | VH CDR 2.4 | FLPGSGST (SEQ ID NO: 8) | | | | |
| | | | VH CDR 3.4 | ATDGNYDWFAY (SEQ ID NO: 9) | | | | |
| | | | VL CDR 1.4 | QSLVHSSGVTY (SEQ ID NO: 10) | mVL.4 | (SEQ ID NO: 15) | hVL.4 | (SEQ ID NO: 24) |
| | | | VL CDR 2.4 | KVS (SEQ ID NO: 5) | | | | |
| | | | VL CDR 3.4 | SQSTHVPPT (SEQ ID NO: 11) | | | | |
| N2 | 1E9A4A4 (I-4376) | MAb15 | | | | | | |
| N2 | 1E9D9B6 | MAb16 | VH CDR 1.16 | GYTFTSYY (SEQ ID NO: 39) | mVH.16 | (SEQ ID NO: 61) | hVH.16a | (SEQ ID NO: 84) |
| | | | VH CDR 2.16 | INPSNGGT (SEQ ID NO: 43) | | | hVH.16b | (SEQ ID NO: 86) |
| | | | VH CDR 3.16 | TRGGYYPFDY (SEQ ID NO: 47) | | | hVH.16c | (SEQ ID NO: 88) |
| | | | VL CDR 1.16 | QSLLDSDGKTY (SEQ ID NO: 50) | mVL.16 | (SEQ ID NO: 65) | hVL.16a | (SEQ ID NO: 85) |
| | | | VL CDR 2.16 | LVS (SEQ ID NO: 53) | | | hVL.16b | (SEQ ID NO: 87) |
| | | | VL CDR 3.16 | WQGTHSPYT (SEQ ID NO: 57) | | | hVL.16c | (SEQ ID NO: 89) |
| N2 | 1C8D10F5 | MAb17 | | | | | | |
| N2 | 1A7C3F11 | MAb18 | | | | | | |
| N2 | 1B3B4F11 | MAb19 | VH CDR 1.19 | GYSITSDYA (SEQ ID NO: 40) | mVH.19 | (SEQ ID NO: 62) | hVH.19a | (SEQ ID NO: 90) |
| | | | VH CDR 2.19 | ISFSGYT (SEQ ID NO: 44) | | | hVH.19b | (SEQ ID NO: 92) |
| | | | VH CDR 3.19 | AREVNYGDSYHFDY (SEQ ID NO: 48) | | | hVH.19c | (SEQ ID NO: 94) |
| | | | VL CDR 1.19 | SQHRTYT (SEQ ID NO: 51) | mVL.19 | (SEQ ID NO: 66) | hVL.19a | (SEQ ID NO: 91) |
| | | | VL CDR 2.19 | VKKDGSH (SEQ ID NO: 54) | | | hVL.19b | (SEQ ID NO: 93) |
| | | | VL CDR 3.19 | GVGDAIKGQSVFV (SEQ ID NO: 58) | | | hVL.19c | (SEQ ID NO: 95) |
| N2 | 1C11F5E8 | MAb20 | | | | | | |

Immunogen N1 = SWKPRSQQPDAPLG-Ahx-Cys-BSA, also represented as (SEQ ID NO: 25)-Ahx-Cys-BSA;
Immunogen N2 = SWKPRSQQPDAPLG-Ahx-Cys-KLH, also represented as (SEQ ID NO: 25)-Ahx-Cys-KLH In Table 3A, all amino acid sequences are represented using conventional N→C orientation. For each immunogen, the progastrin peptide was synthesized with a C-terminal linker of one aminohexanoic acid (Ahx) residue followed by a cysteine (Cys) residue, which was then conjugated to a either a bovine serum albumin ("BSA") or keyhole limpet hemocyanin ("KLH") carrier via the Cys linker residue.

Anti-hPG antibodies obtainable using a peptide antigen having a sequence corresponding to a C-terminal region of hPG, and/or that bind a C-terminal region of hPG, are referred to herein as "C-terminal anti-hPG antibodies." A specific exemplary antigenic region that can be used to construct an immunogen useful for obtaining both polyclonal and monoclonal C-terminal anti-hPG antibodies corresponds to residues 55 to 80 of hPG: QGPWLEEEEEAYGWMDFGRR-SAEDEN (SEQ ID NO:27). Exemplary immunogens including this antigen useful for obtaining C-terminal anti-hPG antibodies, as well as CDR and VH and VL sequences of C-terminal anti-hPG monoclonal antibodies obtained with these exemplary immunogens, are provided in Table 3B, below, and the Examples section.

TABLE 3B

C-Terminal Anti-hPG Monoclonal Antibodies

| Immunogen | Hybridoma (Deposit #) | MAb | Murine CDR Sequences | | mVH and mVL Sequences | hVH and hVL Sequences (projected) |
|---|---|---|---|---|---|---|
| C1 | 1B4A11D11 (I-4371) | MAb5 | | | | |
| C1 | 1B6A11F2 (I-4372) | MAb6 | | | | |
| C1 | 1B11E4B11 (I-4373) | MAb7 | | | | |
| C1 | 1C10D3B9 | MAb8 | VH CDR 1.8 | GFTFTTYA (SEQ ID NO: 37) | mVH.8 (SEQ ID NO: 59) | hVH.8a (SEQ ID NO: 75) |
| | | | VH CDR 2.8 | ISSGGTYT (SEQ ID NO: 41) | | hVH.8b (SEQ ID NO: 77) |
| | | | VH CDR 3.8 | ATQGNYSLDF (SEQ ID NO: 45) | | hVH.8c (SEQ ID NO: 79) |
| | | | VL CDR 1.8 | KSLRHTKGITF (SEQ ID NO: 49) | mVL.8 (SEQ ID NO: 63) | hVL.8a (SEQ ID NO: 76) |
| | | | VL CDR 2.8 | QMS (SEQ ID NO: 52) | | hVL.8b (SEQ ID NO: 78) |
| | | | VL CDR 3.8 | AQNLELPLT (SEQ ID NO: 55) | | hVL.8c (SEQ ID NO: 76) |
| C1 | 1D8F5B3 | MAb9 | | | | |
| C1 | 1E1C7B4 | MAb10 | | | | |
| C1 | 2B4C8C8 (I-4374) | MAb11 | | | | |
| C1 | 2B11E6G4 (I-4375) | MAb12 | | | | |
| C1 | 2C6C3C7 | MAb13 | VH CDR 1.13 | GFIFSSYG (SEQ ID NO: 38) | mVH.13 (SEQ ID NO: 60) | hVH.13a (SEQ ID NO: 80) |
| | | | VH CDR 2.13 | INTFGDRT (SEQ ID NO: 42) | | hVH.13b (SEQ ID NO: 82) |
| | | | VH CDR 3.13 | ARGTGTY (SEQ ID NO: 46) | | |
| | | | VL CDR 1.13 | QSLLDSDGKTY (SEQ ID NO: 50) | mVL.13 (SEQ ID NO: 64) | hVL.13a (SEQ ID NO: 81) |
| | | | VL CDR 2.13 | LVS (SEQ ID NO: 53) | | hVL.13b (SEQ ID NO: 83) |
| | | | VL CDR 3.13 | WQGTHFPQT (SEQ ID NO: 56) | | |
| C1 | 2H9F4B7 | MAb14 | | | | |
| C2 | 1E11E5E10 | MAb21 | | | | |
| C2 | 1F11F5G9 | MAb22 | | | | |
| C2 | 1A11F2C9 | MAb23 | | | | |

TABLE 3B-continued

C-Terminal Anti-hPG Monoclonal Antibodies

| Immunogen | Hybridoma (Deposit #) | MAb | Murine CDR Sequences | mVH and mVL Sequences | hVH and hVL Sequences (projected) |
|---|---|---|---|---|---|

Immunogen C1 = KLH-Cys-Ahx-Ahx-QGPWLEEEEEAYGWMDFGRRSAEDEN, also represented as
KLH-Cys-Ahx Ahx-(SEQ ID NO: 27)
Immunogen C2 = DT-Cys-Ahx-Ahx-QGPWLEEEEEAYGWMDFGRRSAEDEN, also represented as
DT-Cys-Ahx-Ahx-(SEQ ID NO: 27)

In Table 3B, all amino acid sequences are represented using conventional N→C orientation. For each immunogen, the progastrin peptide was synthesized with an N-terminal Ahx-Ahx-Cys linker, which was then conjugated to a either a keyhole limpet hemocyanin ("KLH") or a diphtheria toxin ("DT") carrier via the Cys linker residue.

The specific epitopes bound by the exemplary anti-hPG monoclonal antibodies MAb1-MAb23 provided in Tables 4A and 4B were mapped using the SPOT technique and alanine scanning, as described in Laune et al. (2002) *J. Immunol. Methods* 267:53-70 and Laune (1997) *J. Biol. Chem.* 272: 30937-30944, respectively (see also, Example 6 of the '329 application).

In the SPOT technique, 15 amino acid peptide sequences spanning a putative epitope are generated and spotted onto a nitrocellulose membrane which is then probed with the test antibody to determine the minimal epitope sequence recognized by the antibody. Alanine scanning is used to determine residues within an epitope that are critical for antibody binding. Each residue within a putative epitope is mutated, one by one, to an alanine, and the alanine-containing peptides are then probed with the test antibody.

For N-terminal anti-hPG monoclonal antibodies MAbs #1-4 and 15-20, epitopes comprise at least the following sequences: DAPLG (SEQ ID NO:28), PDAPLG (SEQ ID NO:29), PRSQQPD (SEQ ID NO:30), WKPRSQQPD (SEQ ID NO:31), or WKPRSQQPDAPLG (SEQ ID NO:32), as shown in Table 4A below.

TABLE 4A

| MAb # | PG peptide antigen: SWKPRSQQPDAPLG | SEQ ID NO: |
|---|---|---|
| MAb2 | WKPRSQQPDAPLG | 32 |
| MAb4 | WKPRSQQPDAPLG | 32 |
| MAb1 | PDAPLG | 29 |
| MAb3 | DAPLG | 28 |
| MAb17 | WKPRSQQPD | 31 |
| MAb18 | WKPRSQQPD | 31 |
| MAb19 | WKPRSQQPD | 31 |
| MAb20 | WKPRSQQPD | 31 |
| MAb15 | PRSQQPD | 30 |
| MAb16 | PRSQQPD | 30 |

For C-terminal anti-hPG monoclonal antibodies MAbs #5-7, 9-12, 14 and 21-23, epitopes comprise at least the following sequences: FGRR (SEQ ID NO:33), MDFGR (SEQ ID NO:34), AEDEN (SEQ ID NO:35), and GWMDF-GRR (SEQ ID NO:36), as shown in Table 4B, below.

TABLE 4B

| MAb # | PG peptide antigen: QGPWLEEEEEAYGWMDFGRRSAEDEN | SEQ ID NO: |
|---|---|---|
| MAb14 | GWMDFGRR | 36 |
| MAb11 | MDFGR | 34 |
| MAb5 | FGRR | 33 |
| MAb6 | FGRR | 33 |
| MAb7 | FGRR | 33 |
| MAb9 | FGRR | 33 |
| MAb10 | FGRR..E | 33 |
| MAb12 | FGRR | 33 |
| MAb23 | AEDEN | 35 |

The epitope mapping experiments reveal that anti-hPG MAb2 and MAb4 bind the same epitope; anti-hPG MAb1 and MAb3 bind approximately the same epitope; MAb17, MAb18, MAb19, and MAb20 bind approximately the same epitope; MAb15 and MAb16 bind approximately the same epitope; anti-hPG MAb5, MAb6, MAb7, MAb9, and MAb12 bind the same epitope and bind approximately the same epitope as anti-hPG MAb10; and anti-hPG MAb11 and MAb14 bind approximately the same epitope.

Specific embodiments of N-terminal anti-PG antibodies useful in the methods and kits described herein include antibodies that bind an epitope that includes residues 10 to 14 of hPG (SEQ ID NO:28), residues 9 to 14 of hPG (SEQ ID NO:29), residues 4 to 10 of hPG (SEQ ID NO:30), residues 2 to 10 of hPG (SEQ ID NO:31), or residues 2 to 14 of hPG (SEQ ID NO:32).

Specific embodiments of C-terminal anti-PG antibodies useful in the methods and kits described herein include antibodies that bind an epitope that includes residues 71 to 74 of hPG (SEQ ID NO:33), residues 69 to 73 of hPG (SEQ ID NO:34), residues 76 to 80 of hPG (SEQ ID NO:35), or residues 67 to 74 of hPG (SEQ ID NO:36).

N-terminal and C-terminal anti-hPG antibodies useful in the methods and kits disclosed herein in addition to those provided in Tables 4A & 4B can be identified in competitive binding assays with exemplary MAbs 1-23, or with other reference antibodies that bind N- or C-terminal epitopes, as will be described in more detail in a later section.

Several of the hybridomas useful for obtaining the antibodies were deposited on Oct. 6, 2010 with the Collection Nationale de Cultures de Microorganismes (CNCM) in accordance with the Treaty of Budapest. The designated names of the hybridomas producing anti-hPG MAbs1-23 and the depository registration numbers of those hybridomas deposited are provided in Tables 4A & 4B. In addition, for several of the antibodies, the amino acid sequences of their variable heavy chains (VH), variable light chains (VL), VL complementarity determining regions (CDRs) and VH CDRs have been determined. These amino acid sequences, and the shorthand nomenclature used to reference them throughout the disclosure, are also provided in Tables 4A & 4B. Briefly, murine heavy and light chain variable domains are referred to herein as mVH and mVL followed by the number of the corresponding monoclonal antibody, for example mVH.3 and mVL.3 for the variable light and variable heavy chains of anti-hPG MAb3, respectively. Similarly, human heavy and light chain variable domains are referred to herein as hVH and hVL followed by the number of the corresponding monoclonal antibody. The three variable heavy chain CDRs and three variable light chain CDRs are referred to as VH CDR 1, 2, or 3, and VL CDR 1, 2, or 3, respectively, followed by the number of the specific anti-hPG monoclonal antibody. For example, VH CDR 1 of MAb3 is denoted VH CDR 1.3 and VL CDR 1 of MAb3 is denoted VL CDR 1.3. VH CDR 2 of MAb3 is denoted VH CDR 2.3, and VL CDR 2 of MAb3 is denoted VL CDR 2.3.

It is expected that corresponding CDRs and/or VH and VL chains of anti-hPG monoclonal antibodies that bind approximately the same epitopes could be interchanged to yield new anti-hPG monoclonal antibodies useful in the methods and kits described herein. For example, as noted above, exemplary anti-hPG monoclonal antibodies MAb5 and MAb6 bind the same epitope. An anti-hPG monoclonal antibody can be designed that includes, in its VL chain, various combinations of the VL CDRs of these two antibodies, and/or in its VH chain various combinations of the VH CDRs of these two antibodies. As a specific non-limiting example to illustrate the various combinations possible, such an antibody could include in its VL chain, CDRs 1 and 2 of MAb5 (VL CDR 1.5 and VL CDR 2.5, respectively) and CDR 3 of MAb6 (VL CDR 3.6), and in its VH chain, CDR 1 of MAb6 (VH CDR 1.6) and CDRs 2 and 3 of MAb5 (VH CDR 2.5 and VH CDR 3.5, respectively) Amino acid sequences of CDRs of antibodies produced by hybridomas that have been deposited can be obtained using conventional means. See, e.g., Coligan (1996) *Current Protocols in Immunology*, Vol. 3, New York: John Wiley and Sons.

With reference to Table 3A, specific embodiments of N-terminal anti-hPG antibodies useful in the methods and kits described herein include, but are not limited to, the following:

(a) antibodies having VL CDRs that correspond in sequence to the VL CDRs of MAb1, MAb2, MAb3, MAb4, MAb15, MAb16, MAb17, MAb18, MAb19 or MAb20, and VH CDRs that correspond in sequence to the VH CDRs of MAb1, MAb2, MAb3, MAb4, MAb15, MAb16, MAb17, MAb18, MAb19 or MAb20;

(b) antibodies having VL CDRs and VH CDRs that correspond in sequence to the VL and VH CDRs of MAb1, MAb2, MAb3, MAb4, MAb15, MAb16, MAb17, MAb18, MAb19 or MAb20;

(c) antibodies in which:
  (i) VL CDR 1 is selected from QSIVHSNGNTY ("VL CDR 1.3"; SEQ ID NO:4), QSLVHSSGVTY ("VL CDR 1.4"; SEQ ID NO:10), QSLLDSDGKTY ("VL CDR 1.16"; SEQ ID NO:50), and SQHRTYT ("VL CDR 1.19"; SEQ ID NO:51);
  (ii) VL CDR2 is selected from KVS ("VL CDR 2.3" and "VL CDR 2.4"; SEQ ID NO:5), LVS ("VL CDR 2.16"; SEQ ID NO:53), and VKKDGSH ("VL CDR 2.19"; SEQ ID NO:54);
  (iii) VL CDR3 is selected from FQGSHVPFT ("VL CDR 3.3"; SEQ ID NO:6), SQSTHVPPT ("VL CDR 3.4"; SEQ ID NO:11), WQGTHSPYT ("VL CDR 3.16"; SEQ ID NO:57), and GVGDAIKGQSVFV ("VL CDR 3.19"; SEQ ID NO:58);
  (iv) VH CDR1 is selected from GYIFTSYW ("VH CDR 1.3"; SEQ ID NO:1), GYTFSSSW ("VH CDR 1.4"; SEQ ID NO:7), GYTFTSYY ("VH CDR 1.16"; SEQ ID NO:39), and GYSITSDYA ("VH CDR 1.19"; SEQ ID NO:40);
  (v) VH CDR2 is selected from FYPGNSDS ("VH CDR 2.3"; SEQ ID NO:2), FLPGSGST ("VH CDR 2.4"; SEQ ID NO:8), INPSNGGT ("VH CDR 2.16"; SEQ ID NO:43), and ISFSGYT ("VH CDR 2.19"; SEQ ID NO:44); and
  (vi) VH CDR3 is selected from TRRDSPQY ("VH CDR 3.3"; SEQ ID NO:3), ATDGNYDWFAY ("VH CDR 3.4" SEQ ID NO:9), TRGGYYPFDY ("VH CDR 3.16"; SEQ ID NO:47), and AREVNYGDSYHFDY ("VH CDR 3.19"; SEQ ID NO:48);

(d) antibodies having a VL that corresponds in sequence to the VL of MAb1, MAb2, MAb3, MAb4, MAb15, MAb16, MAb17, MAb18, MAb19 or MAb20 and a VH that corresponds in sequence to the VH of MAb1, MAb2, MAb3, MAb4, MAb15, MAb16, MAb17, MAb18, MAb19 or MAb20; and (e) antibodies having a VL and a VH that corresponds in sequence to the VL and VH of MAb1, MAb2, MAb3, MAb4, MAb15, MAb16, MAb17, MAb18, MAb19 or MAb20.

With reference to Table 3B, specific embodiments of C-terminal anti-hPG antibodies useful in the methods and kits described herein include, but are not limited to, the following:

(f) antibodies having VL CDRs that correspond in sequence to the VL CDRs of MAb5, MAb6, MAb7, MAb8, MAb9, MAb10, MAb11, MAb12, MAb13, MAb14, MAb21, MAb22 or MAb23 and VH CDRs that correspond in sequence to the VH CDRs of MBb5, MAb6, MAb7, MAB8, MAB9, MAb10, MAb11, MAb12, MAb13, MAb14, MAb21, MAb22 or MAb23;

(g) antibodies having VL CDRs and VH CDRs that correspond in sequence to the VL and VH CDRs of MAb5, MAb6, MAb7, MAb8, MAb9, MAb10, MAb11, MAb12, MAb13, MAb14, MAb21, MAb22 or MAb23;

(h) antibodies in which:
  (i) VL CDR1 is selected from KSLRHTKGITF ("VL CDR 1.8"; SEQ ID NO:49) and QSLLDSDGKTY ("VL CDR 1.13"; SEQ ID NO:50);
  (ii) VL CDR2 is selected from QMS ("VL CDR 2.8"; SEQ ID NO:52) and LVS ("VL CDR 2.13"; SEQ ID NO:53);
  (iii) VL CDR 3 is selected from AQNLELPLT ("VL CDR 3.8"; SEQ ID NO:55) and WQGTHFPQT ("VL CDR 3.13"; SEQ ID NO:56);
  (iv) VH CDR1 is selected from GFTFTTYA ("VH CDR 1.8"; SEQ ID NO:37) and GFIFSSYG ("VH CDR 1.13"; SEQ ID NO:38);
  (v) VH CDR2 is selected from ISSGGTYT ("VH CDR 2.8"; SEQ ID NO:41) and INTFGDRT ("VH CDR 2.13"; SEQ ID NO:42); and
  (vi) VH CDR3 is selected from ATQGNYSLDF ("VH CDR 3.8"; SEQ ID NO:45) and ARGTGTY ("VH CDR 3.13"; SEQ ID NO:46);

(i) antibodies having a VL that corresponds in sequence to the VL of MAb5, MAb6, MAb7, MAb8, MAb9, MAb10, MAb11, MAb12, MAb13, MAb14, MAb21, MAb22or MAb23 and a VH that corresponds in sequence to the VH of MAb5, MAb6, MAb7, MAb8, MAb9, MAb10, MAb11, MAb12, MAb13, MAb14, MAb21, MAb22 or MAb23; and (j) antibodies having a VL and a VH that correspond in sequence to the VL and VH that correspond in sequence to the VL and VH of MAb5, MAb6, MAb7, MAb8, MAb9, MAb10, MAb11, MAb12, MAb13, MAb14, MAb21, MAb22 or MAb23.

As noted in Tables 4A & 4B, several N-terminal and C-terminal monoclonal anti-hPG antibodies have been identified. All of these antibodies are specific for hPG, and all but MAb14 exhibit neutralizing activity on colorectal cancer cells. Although neutralizing activity may be important for therapeutic applications, it is not necessary for the diagnostic purposes of this disclosure. Thus, both non-neutralizing and neutralizing antibodies that specifically bind hPG are useful for the various diagnostic methods described herein.

The affinity of an anti hPG antibody is not critical to the diagnostic methods of the disclosure, but high affinity antibodies improve the sensitivity of progastrin detection. Furthermore, high affinity antibodies are necessary for therapeutic applications. Accordingly, there may be advantages to using antibodies exhibiting affinities of at least about 1 nM; for example, an affinity of at least about 90 nM, 80 nM, 70 nM, 60 nM, 50 nM, 40 nM, 30 nM, 20 nM, 15 nM, 10 nM, 7 nM, 6 nM, 5 nM, 4 nM, 3 nM, 2 nM, 1 nM, 0.1 nM, 0.01 nM, 0.001 nM or even greater.

The measured affinities of the anti-hPG monoclonal antibodies identified in Tables 4A & 4B range from $10^{-6}$ to $10^{-12}$ M, as noted in Table 5, below:

TABLE 5

| Monoclonal Antibody | Affinity constant measured $K_D$ (M) |
|---|---|
| Anti-hPG MAb 1 | 2.5 µM ($2.5 \times 10^{-6}$M) |
| Anti-hPG MAb 2 | 185 nM ($1.85 \times 10^{-7}$M) |
| Anti-hPG MAb 3 | 6.4 nM ($6.4 \times 10^{-9}$M) |
| Anti-hPG MAb 4 | 3.5 nM ($3.5 \times 10^{-9}$M) |
| Anti-hPG MAb 5 | 13 pM ($1.30 \times 10^{-11}$M) |
| Anti-hPG MAb 6 | 0.6 nM ($6.38 \times 10^{-10}$M) |
| Anti-hPG MAb 7 | 58 pM ($5.84 \times 10^{-11}$M) |
| Anti-hPG MAb 8 | 0.1 nM ($1.08 \times 10^{-10}$M) |
| Anti-hPG MAb 10 | 3.6 nM ($3.62 \times 10^{-9}$M) |
| Anti-hPG MAb 11 | 0.3 nM ($3.12 \times 10^{-10}$M) |
| Anti-hPG MAb 12 | 0.4 nM ($4.43 \times 10^{-10}$M) |
| Anti-hPG MAb 13 | 0.6 nM ($6.12 \times 10^{-10}$M) |
| Anti-hPG MAb 14 | 6.8 pM ($6.86 \times 10^{-12}$M) |
| Anti-hPG MAb 15 | 0.2 nM ($2.11 \times 10^{-10}$M) |
| Anti-hPG MAb 16 | 0.2 nM ($2.78 \times 10^{-10}$M) |
| Anti-hPG MAb 17 | 8.3 nM ($8.29 \times 10^{-9}$M) |
| Anti-hPG MAb 18 | 1.2 nM ($1.24 \times 10^{-9}$M) |
| Anti-hPG MAb 19 | 0.7 nM ($7.79 \times 10^{-10}$M) |
| Anti-hPG MAb 20 | 0.2 nM ($2.47 \times 10^{-10}$M) |
| Anti-hPG MAb 21 | 3.9 nM ($3.90 \times 10^{-9}$M) |
| Anti-hPG MAb 22 | 5 nM ($4.94 \times 10^{-9}$M) |
| Anti-hPG MAb 23 | 0.4 µM ($3.99 \times 10^{-7}$M) |

An anti-PG monoclonal antibody having an affinity especially suited for a particular desired application can be readily selected from amongst these, or generated or designed using the various immunogens, complementarity determining region (CDR) sequences, variable heavy (VH) and variable light (VL) chain sequences of anti-hPG antibodies described herein. The affinity of any particular anti-PG monoclonal antibody can be determined using techniques well known in the art or described herein, such as for example, ELISA, isothermal titration calorimetry (ITC), BIAcore, or fluorescent polarization assays. A specific assay is provided in Example 5.

As will be recognized by skilled artisans, anti-hPG antibodies having specific binding properties, such as the ability to bind a specific epitope of interest, can be readily obtained using the various antigens and immunogens described herein and assessing their ability to compete for binding hPG with a reference antibody of interest. Any of the anti-hPG antibodies described herein can be utilized as a reference antibody in such a competition assay. A specific assay useful for assessing the ability of an antibody to compete for binding hPG with a biotinylated reference anti-hPG antibody of interest is provided in Example 6.

In conducting an antibody competition study between a reference anti-hPG antibody and any test antibody (irrespective of species or isotype), one may first label the reference with a label detectable either directly, such as, for example, a radioisotope or fluorophore, or indirectly, such as, for example biotin (detectable via binding with fluorescently-labeled streptavidin) or an enzyme (detectable via an enzymatic reaction), to enable subsequent identification. In this case, a labeled reference anti-hPG antibody (in fixed or increasing concentrations) is incubated with a known amount of hPG, forming a hPG-labeled anti-hPG antibody complex. The unlabeled test antibody is then added to the complex. The intensity of the complexed label is measured. If the test antibody competes with the labeled reference anti-hPG antibody for hPG by binding to an overlapping epitope, the intensity of the complexed label will be decrease relative to a control experiment carried out in the absence of test antibody.

Numerous methods for carrying out binding competition assays are known and can be adapted to yield results comparable to the assay described above and in Example 6.

An antibody is considered to compete for binding hPG with a reference anti-hPG antibody, and thus considered to bind approximately the same or an overlapping epitope of hPG as the reference anti-hPG antibody, if it reduces binding of the reference anti-hPG antibody to hPG in a competitive binding assay, and specifically the competitive binding assay of Example 6, by at least 50%, at a test antibody concentration in the range of 0.01 to 100 µg/mL (e.g., 0.01 µg/mL, 0.08 µg/mL, 0.4 µg/mL, 2 µg/mL, 10 µg/mL, 50 µg/mL or 100 µg/mL or other concentration within the stated range), although higher levels of reduction, for example, 60%, 70%, 80%, 90% or even 100%, may be desirable As will be appreciated by skilled artisans, anti-hPG antibodies useful in the diagnostic methods can be of any origin, including, for example, mammalian (e.g., human, primate, rodent, goat or rabbit), non-mammalian, chimeric in nature (derived from more than one species of origin) and/or CDR-grafted (e.g., humanized).

Methods for humanizing antibodies, including methods for designing humanized antibodies, are also well-known in the art. See, e.g., Lefranc et al. (2003) *Dev. Comp. Immunol.* 27:55-77; Lefranc et al. (2009) *Nucl. Acids Res.* 37:D1006-1012; Lefranc (2008) *Mol. Biotechnol.* 40:101-111; Riechmann et al. (1988) *Nature* 332:323-7; U.S. Pat. Nos. 5,530,101, 5,585,089, 5,693,761, 5,693,762 and 6,180,370 to Queen et al.; EP239400; PCT publication WO 91/09967; U.S. Pat. No. 5,225,539; EP592106; EP519596; Padlan (1991) *Mol. Immunol.* 28:489-498; Studnicka et al. (1994) *Prot. Eng.* 7:805-814; Roguska et al. (1994) *Proc. Natl. Acad. Sci.* 91:969-973; and U.S. Pat. No. 5,565,332, the disclosures of which are hereby incorporated by reference in their entireties.

Humanized versions of antibodies having CDR sequences corresponding to the CDRs of non-human anti-hPG antibodies, including by way of example and not limitation, the various N-terminal anti-hPG monoclonal antibodies provided in Table 3A and the various C-terminal anti-hPG monoclonal antibodies provided in Table 3B, can be obtained using these well-known methods. Projected sequences for humanized VL and VH chains of selected anti-hPG antibodies are provided in Tables 4A and 4B. Either murine or humanized antibodies may be used for the diagnostic purposes of the disclosure. Specific examples of humanized antibodies include antibodies comprising:

(a) any three VL CDRs and any three VH CDRs disclosed herein;

(b) a heavy chain variable region comprising an amino acid sequence corresponding to SEQ ID NO:21 and a light chain variable region comprising an amino acid sequence corresponding to SEQ ID NO:22;

(c) a heavy chain variable region comprising an amino acid sequence corresponding to SEQ ID NO:23 and a light chain variable region comprising an amino acid sequence corresponding to SEQ ID NO:24;

(d) a heavy chain variable region comprising an amino acid sequence selected from the group consisting of SEQ ID NO:75, 77, and 79 and a light chain variable region comprising an amino acid sequence selected from the group consisting of SEQ ID NO:76 and 78;

(e) a heavy chain variable region comprising an amino acid sequence selected from the group consisting of SEQ ID NO:80 and 82 and a light chain variable region comprising an amino acid sequence selected from the group consisting of SEQ ID NO:81 and 83;

(f) a heavy chain variable region comprising an amino acid sequence selected from the group consisting of SEQ ID NO:84, 86, and 88 and a light chain variable region comprising an amino acid sequence selected from the group consisting of SEQ ID NO:85, 87, and 89; and (g) a heavy chain variable region comprising an amino acid sequence selected from the group consisting of SEQ ID NO:90, 92, and 94 and a light chain variable region comprising an amino acid sequence selected from the group consisting of SEQ ID NO:91, 93, and 95.

The anti-PG monoclonal antibodies and antibody fragments used in the methods of the present disclosure can be derivatized, e.g., covalently modified or conjugated to other molecules.

In certain embodiments, the anti-PG antibodies or fragments thereof are conjugated to a diagnostic agent. Detection of an anti-PG antibody-bound hPG can be facilitated by coupling the antibody to a substance that can be detected directly or indirectly. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions.

The detectable substance may be coupled or conjugated either directly to the antibody (or fragment thereof) or indirectly, through an intermediate (such as, for example, a linker known in the art) using techniques known in the art.

Examples of suitable enzymes include horseradish peroxidase, alkaline phosphatase, beta-galactosidase, or acetylcholinesterase. Bioluminescent, chemiluminescent and/or chromogenic substrates for these enzymes are known in the art. For example, when the enzyme is alkaline phosphatase, the substrate may include chemiluminescent substrates such as AMPPD® (3-(2'-spiroadamantane)-4-methoxy-4-(3''-phosphoryloxy)phenyl-1,2-dioxetane), CDP-star® (disodium 4-chloro-3-(methoxyspiro{1,2-dioxetane-3,2'-(5'-chloro)tricyclo[3.3.1.1$^{3,7}$]decan}-4-yl)phenyl phosphate) and CSPD® (disodium 3-(4-methoxyspiro{1,2-dioxetane-3,2-(5'-chloro)tricyclo[3.3.1.1$^{3,7}$]decan}-4-yl)phenyl phosphate); chromogenic substrates such as p-nitrophenyl phosphate, 5-bromo-4-chloro-3-indolyl-phosphate (BCIP), 4-nitroblue tetrazolium chloride (NBT) and iodo nitro tetrazolium (INT) and the like.

Examples of metal ions that can be conjugated to anti-hPG antibodies for use in the diagnostic methods of the disclosure are disclosed in U.S. Pat. No. 4,741,900. Examples of suitable prosthetic group complexes include streptavidin/biotin and avidin/biotin. Examples of suitable fluorescent materials include umbelliferone, fluorescein, fluorescein isothiocyanate, rhodamine, dichlorotriazinylamine fluorescein, dansyl chloride or phycoerythrin. An example of a luminescent material is luminol Examples of bioluminescent materials include luciferase, luciferin, and aequorin. Examples of suitable radioactive material include $^{125}$I, $^{131}$I, $^{111}$In or $^{99}$Tc.

Methods of coupling antibodies to detectable substrates are known in the art. Typical techniques are described by Kennedy et al., (1976) *Clin. Chim. Acta* 70:1-31); Schurs et al. (1977) *Clin. Chim Acta* 81:1-40; *Antibodies: A Laboratory Manual* Harlow & Lane, eds., Cold Spring Harbor Laboratory Press (1988) at ch. 9; *Bioconjugate Techniques*, Hermanson, Academic Press (2008).

Antibodies may also be attached to solid supports, which are particularly useful for immunoassays or purification of hPG. Such solid supports include, but are not limited to, glass, cellulose, polyacrylamide, nylon, polystyrene, polyvinyl chloride or polypropylene.

Although the various anti-hPG antibodies useful in the methods and kits described herein have been exemplified with full length antibodies, skilled artisans will appreciate that binding fragments, or surrogate antibodies designed or derived from full-length antibodies or binding fragments, may also be used. Suitable fragments, surrogates, etc., include, but are not limited to, Fab', F(ab')$_2$, Fab, Fv, vIgG, scFv fragments and surrobodies.

6.5. Kits

In an aspect of the disclosure, kits are provided for use in diagnostic and research applications as suggested above. In some embodiments, a kit is provided comprising anti-hPG antibodies and reagents necessary to detect and/or quantify hPG in a sample and can include assay reagents and buffers. In addition, the kits can include instructional materials containing instructions (e.g., protocols) for the practice of diagnostic methods. While the instructional materials typically comprise written or printed materials, they are not limited to such. A medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. Such media can include addresses to Internet sites that provide such instructional materials.

The kits can be adapted for the diagnosis or screening of patients already diagnosed with one or more conditions. For example, the kit can contain instructional materials for patients diagnosed with hepatitis C, so that a diagnosis of additional liver pathologies based on hPG levels can be made. The materials can also be directed to patients diagnosed with other liver conditions such as cirrhosis and/or liver cancer. The kits can also be adapted for the screening of high-risk populations, including populations where hepatitis C or other liver pathologies are more prevalent.

6.6. Automated Methods and Implementations

In some embodiments of the disclosure, the method of diagnosing or determining an indicated risk for one or more liver pathologies is implemented in whole or in part by a machine. For example, the method can be practiced by a diagnostic unit comprising a blood sample input. The blood sample is then manipulated by the machine to produce a progastrin level. Such manipulation can include binding of progastrin in the blood sample with one or more antibodies. The progastrin-antibody sample can comprise a detectable marker. Measurement of the detectable marker provides a data output that can be delivered to a display. Alternatively, the data output can be correlated by a computer according to the progastrin level with one or more liver pathologies. In another embodiment, the data output can be compared with a threshold value of hPG, for example 400, 450, 500, 550, 600, 650, or 700 pM. If the determined hPG level is above the threshold, a diagnosis of one or more liver pathologies is made.

The computer can further comprise a database of statistical or experiential information. The information can be used to correlate the quantified progastrin level and additional data which can be inputted by a user to provide a more detailed or accurate diagnosis or indication of risk of one or more liver pathologies. The database can also comprise information as to recommended treatment or further diagnostic options. Accordingly, the methods of the disclosure can be implemented in the form of a computerized medical diagnostic method. Exemplary automated systems useful for implementing the assay diagnostics of the present disclosure include those described in U.S. Pat. Nos. 6,063,026, 6,063,340, and 7,381,370.

In general, such automated systems can comprise one or more of the following: blood or sample input units, blood or sample manipulation units, hPG and/or hPG marker detection units, a CPU with storage for one or more databases, a display and/or communication unit, or units combining the functionality of any one of the previous units. The units are integrated to receive a sample, process the sample using reagents to provide a detectable marker indicative of hPG levels, detect the level of marker, correlate the level of marker with a hPG level, and provide an output of the information, namely the determined hPG level and optionally a diagnosis based on the determined hPG level. The units can also integrate with a CPU and database to provide additional information such as a diagnosis of liver cancer, hepatitis C, cirrhosis, or a combination thereof based on the determined hPG level and optional additional information provided by the automated assay or inputted by a user. In some aspects, the units can integrate with non-automated methods. For example, a partially automated method can comprise units for receiving and manipulating sample. The manipulated sample can then be submitted to testing by way of a non-automated method.

7. EXAMPLES

Example 1

Quantification of Plasma Progastrin 96-well microtiter plates are coated with between 0.5 and 10 μg/mL of a C-terminal anti-hPG antibody, for example, a rabbit C-terminal anti-hPG polyclonal antibody, and then incubated overnight. Plates are then washed three times in PBS-Tween (0.05%) and blocked with 2% (w/v) nonfat dried milk in PBS-Tween (0.05%). Separately, test samples, control samples (blank or PG-negative plasma or serum samples), and between about 5 pM ($0.5 \times 10^{-11}$ M) and about 0.1 nM ($1 \times 10^{-10}$ M) of an hPG reference standard (lyophilized hPG diluted in PG-negative plasma or serum) are prepared in an appropriate diluent (e.g., PBS-Tween 0.05%). Samples are incubated on the coated plates for between 2 and 4 hours at 37° C., or alternatively between 12 and 16 hours at 21° C. After incubation, plates are washed three times with PBS-Tween (0.05%) and incubated with between 0.001 and 0.1 μg/mL of an N-terminal anti-hPG monoclonal antibody as described herein, coupled to horseradish peroxidase (HRP) (Nakane et al., 1974, *J. Histochem. Cytochem.* 22(12):1084-1091) for 30 minutes at 21° C. Plates are then washed three times in PBS-Tween (0.05%) and HRP substrate is added for 15 minutes at 21° C. The reaction is stopped by added 100 μL of 0.5M sulfuric acid and an optical density measurement is taken at 405 nm. Test sample hPG levels are determined by comparison to a standard curve constructed from the measurements derived from the hPG reference standard.

Other assays for competition are known and can be adapted to yield comparable results to the assay described above.

Example 2

Identification of an Increased Risk of or Diagnosis of One or More Liver Pathologies in a Patient A patient who is suspected of having a liver pathology, or a patient who is undergoing screening, e.g., a screening done as part of a routine physical, provides a biological sample such as plasma, serum or blood. The progastrin levels are quantified, for example, as shown in Example 1, to produce a number that corresponds to the progastrin concentration in the blood sample. In the methods of the disclosure, the number is generally within 1% to 5% (or less) of the true progastrin number, as assays specific for progastrin and not its precursors or products are used. This number is then compared to a listing of liver pathologies associated with progastrin levels within a defined range. In other words, progastrin levels indicative of certain liver pathologies are compared to the quantified number. Certain sub-ranges can indicate differing levels of risk. For example, a low but elevated level of progastrin can indicate a moderate risk of one or more pathologies, whereas a high level of progastrin can indicate a high risk of one or more pathologies. The level can be compared with a threshold value, thereby producing a positive or negative test result. Optionally, a second biomarker can be tested to confirm a diagnosis or indication. For example, a patient who presents with a moderate risk of a liver pathology, but not a high risk, can have a second biomarker tested. If the second biomarker also indicates the same liver pathology, then a diagnosis of that pathology is more likely to be accurate. The means for determining progastrin levels can be provided in a kit. The kit can also provide statistical or other data correlating progastrin levels with one or more pathologies, particularly liver pathologies, and as optional supplemented by one or more additional biomarkers.

Patients who have already been diagnosed with a liver pathology can also undergo hPG testing. For example, a patient diagnosed with liver cancer can undergo hPG testing to determine whether the patient also has additional liver pathologies such as hepatitis C and cirrhosis. Because hepatitis C levels are not normally elevated except in the case where a patient presents with multiple liver pathologies, e.g., liver cancer, cirrhosis, and hepatitis C, progastrin is a useful biomarker for the diagnosis of hepatitis C in such patients. Likewise, patients already diagnosed with hepatitis C or cirrhosis can be screened for additional pathologies by determining whether hPG levels are abnormal.

hPG levels can be used in some instances to confirm a diagnosis. For example, a patient who presents with abnormal test results for one or more biomarkers indicative of liver cancer or another liver pathology, can be screened for abnormally high levels of hPG to confirm the initial diagnosis. hPG levels can be quantified in at-risk populations as part of routine screening program. For example, because very high hPG levels are correlated with multiple liver pathologies and because patients presenting with hepatitis C typically co-present with at least one other liver pathology, populations with high levels of hepatitis C are likely candidates for hPG screening. hPG levels can also be used to monitor the course of treatment of one or more liver pathologies. Decreasing hPG levels would be correlated with effective treatment.

Example 3

Kits, Units, Tests, and Diagnostics for the Diagnosis of One or More Liver Pathologies Articles comprising one or more diagnostics can be utilized in the methods of diagnosis described herein. For example, a blotter or chromatographic strip can be adapted to change color upon binding with blood or blood components from a patient wherein the progastrin level is above a threshold value. Alternatively, the kit can comprise reagents for binding a marker to progastrin in blood. Such a marker can be, for example, a radioisotope or chromophore. Detection and quantification of radiation (induced by excitation or otherwise) can then be used to generate a positive test result if the marker emission is of sufficient intensity to indicate progastrin levels above a threshold. Test results can be adapted to indicate ranges, such as risk values. For example, a kit can comprise a test adapted to display a first signal for one range of progastrin levels and additional signals for other ranges of progastrin levels.

In a particular example, a diagnostic unit or system comprises one or more sample chambers for manipulation of a blood sample, either by a technician or by an automated mechanism. The unit or system further comprises one or more reagents, such as antibodies that specifically bind to progastrin. In a unit or system for the specific assaying of progastrin, a sandwich assay can be performed using a plurality of antibodies provided in the unit or system. The system or unit can comprise a detector for detecting the amount of a marker used to quantify the level of bound-progastrin. The system or unit can further comprise a processor such as a computer programmed with instructions to correlate the level of detected marker with a level of bound-progastrin and to correlate a level of bound-progastrin with a diagnosis. Finally, the system or unit can comprise a unit for displaying or communicating the test results and/or diagnosis. In an alternative unit or system, the unit comprises a blood sample repository and one or more reagents that bind to progastrin. For example, a test strip impregnated or coated with reagents which contact progastrin and result in a color change can be used to provide a one-drop liver pathology test.

Example 4

ELISA Assay for Assessing Specificity of Anti-hPG Antibodies

Specificity of anti-hPG antibodies can be conveniently determined using an ELISA assays as follows. 96-well plates are incubated overnight at 4° C. with appropriate concentration(s) of test polypeptide (e.g., 25 and 50 ng recombinant human PG, and 50 and 250 ng CTFP or other gastrin-derived gene products) in Phosphate-Buffered Saline (PBS), after which the wells are washed three times with wash solution (PBS and 0.1% Tween-20), and then incubated for 2 hours at 22° C. with 100 µL blocking solution (PBS, 0.1% Tween-20, 0.1% Bovine Serum Albumin or casein hydrolysate) per well. After blocking, the wells are washed three times and the antibody to be assayed (test antibody) is added. 100 µL of the test antibody (at 0.3 to 1 ng/mL) in PBS and 0.1% Tween-20 are added to each well. Plates are then incubated for 2 hours at 22° C., after which the test antibody solution is discarded and replaced, after a wash step (3×100 µL wash solution, as noted above), with blocking solution containing a secondary antibody, a goat anti-mouse IgG (Fc) antibody coupled to horseradish peroxidase. After a 1-hour incubation with secondary antibody, 100 µL of substrate solution (e.g., Fast OPD, or O-phenylenediamine dihydrochloride, available from Sigma-Aldrich Co., prepared according to manufacturer's directions) is added to each well and incubated in the dark for 20 minutes at 22° C. The reaction is stopped by adding 50 µL of 4N sulfuric acid and the amount of substrate catalyzed determined by measuring the optical density (O.D.) at 492 nm. Substrate conversion is proportional to the amount of primary (test) antibody bound to the antigen. Experiments are run in duplicate and OD measurements plotted as a function of antigen concentration. Test antibodies are scored as highly specific for PG if the measured O.D. is between 0.2 and 1.5 for hPG and there is no statistically significant signal above background with CTFP or any of the other gastrin-gene derived peptides, where the background is the average signal from control wells containing only PBS.

Example 5

Assay for Assessing Affinity of an Anti-hPG Antibody

Affinity constants of anti-hPG antibodies can be measured using the Proteon Technique (BioRad), according to Nahshol et al. (2008) *Analytical Biochemistry* 383:52-60, hereby incorporated by reference in its entirety. Briefly, for murine anti-PG antibodies, an anti-mouse IgG antibody (50 µg/mL) is first coated on a sensor chip, making sure that the signal detected by the chip after injection of the antibody falls between 10,000 and 11,500 response units (RU). The murine anti-hPG antibody of interest (test antibody) is then injected (at a typical concentration of 30 µg/mL). If the test antibody binds sufficiently, and additional signal of at least 500 RU will be observed. A time-course of binding between test antibody and hPG is then obtained by injecting varying concentrations of hPG, for example 200 nM, 100 nM, 50 nM, 25 nM, and 12.5 nM, and detecting the level of association. Typically, several channels are available to test multiple antibodies in parallel in a single experiment, making it possible to assay binding of a single test antibody at different concentrations of hPG in parallel. One channel should be injected with a murine monoclonal antibody that is not specific to hPG as a control for non-specific binding and another channel should be injected with dilution buffer alone as a baseline for the background signal. Generally, no binding is detectable in the channel injected with non-specific murine antibody. Antibodies displaying a high level of association in this setting, which may result in saturation of the trapped monoclonal antibody by hPG, can be tested against lower hPG concentrations (50 nM, 25 nM, 12.5 nM, 6.25 nM and 3.125 nM), allowing for a more refined measurement.

Affinity constants ($K_D$) are calculated as the ratio between the dissociation constant ($k_d$) and the association constant ($k_a$). Experimental values can be validated by analyzing the statistically relevant similarity between experimental curves based on binding measurements and theoretical profiles.

Affinity constants of non-murine anti-hPG antibodies can be assessed in a similar format using an IgG specific for the species of origin of the anti-hPG test antibody.

Example 6

Assay for Assessing Competitive Binding with a Reference Anti-hPG Antibody

An assay with specificity for assessing whether an antibody of interest (test antibody) competes for binding hPG with a biotinylated reference anti-hPG antibody can be performed as follows. 96-well plates are coated with a capture anti-hPG antibody (polyclonal or monoclonal antibody recognizing an N-or C-terminal region of hPG that differs from the epitope recognized by the biotinylated reference anti-hPG antibody), at a concentration to be chosen within the range of 1-10 µg/mL, overnight at 4° C. (0.1 to 1 µg/well). After blocking with blocking buffer (0.1% Tween-20, 0.1% BSA in PBS) for 2 hr at 22° C., recombinant hPG is added at a concentration ranging between 10 pM to 1 nM (10 to 1000 pg/well) and incubated for 2 hr at 22° C. Thereafter, the biotinylated reference anti-hPG antibody (or a mixture containing the biotinylated reference anti-hPG antibody) is added, along with increasing concentrations of unlabeled test antibody, and incubated for 1 hr at 22° C. After washing to remove unbound antibodies, detection of bound labeled reference anti-hPG antibody is performed by incubating the mixture with 50 ng/mL steptavidin-HRP for 1 hr at 22° C., followed by incubation with a fluorogenic substrate for horseradish peroxidase and quantification of the relative light units (RLU) in a luminometer. Assays are performed in duplicate.

Antibodies that compete with a reference anti-hPG antibody inhibit the binding of the reference antibody to hPG. An antibody that binds to substantially the same epitope, or with an overlapping epitope, as the reference antibody significantly reduces (for example, by at least 50%) the amount of reference anti-hPG antibody bound, as evidenced by a reduction observed RLUs.

A high control value is obtained from a control experiment carried out by incubating the labeled reference antibody with recombinant hPG without test antibody. A low control value is obtained from a control experiment carried out by incubating the labeled reference antibody with recombinant hPG in the presence of excess concentrations of the unlabeled reference antibody (the unlabeled reference antibody thus competing with the labeled antibody for binding to hPG). The capacity of test antibodies to compete with the reference anti-hPG antibody is then determined by incubating the labeled reference antibody with recombinant hPG in the presence of increasing concentrations of the unlabeled test antibody In a test assay, a significant reduction in the observed RLUs in the presence of a test antibody indicates that the test antibody recognizes substantially the same epitope as the reference anti-hPG antibody.

The inhibition of binding can be expressed as an inhibition constant, or $K_i$, which is calculated according to the following formula:

$$K_i = \frac{IC_{50}}{1 + \left[\frac{R_c}{K_d}\right]}$$

where "$IC_{50}$" is the concentration of test antibody that yields a 50% reduction in binding of the reference antibody, $R_c$ is the reference anti-hPG Ab concentration and $K_D$ is the dissociation constant of the reference anti-hPG antibody, a measure of its affinity for hPG. Useful test antibodies that compete with a reference anti-hPG antibody (for example, one of the anti-hPG antibodies described herein) will typically have $K_i$s ranging from 10 pM to 100 nM under assay conditions described herein.

All publications, patents, patent applications and other documents cited in this application are hereby incorporated by reference in their entireties for all purposes to the same extent as if each individual publication, patent, patent application or other document were individually indicated to be incorporated by reference for all purposes. While various specific embodiments have been illustrated and described, it will be appreciated that various changes can be made without departing from the spirit and scope of the invention(s).

What is claimed is:

1. A method of diagnosing whether a subject suffers from liver cancer and at least one other liver pathology selected from hepatitis C and cirrhosis, comprising the steps of:
   (a) identifying, using an anti-hPG antibody, whether said subject previously diagnosed with liver cancer has a serum or plasma human progastrin (hPG) concentration above a threshold value, where the threshold value is at least about 100 pM, and
   (b) testing said patient for at least one other liver pathology selected from hepatitis C and cirrhosis,
   thereby diagnosing whether the subject suffers from liver cancer and at least one other liver pathology selected from hepatitis C and cirrhosis.

2. The method of claim 1, in which the threshold value is 400 pM.

3. The method of claim 1, in which the threshold value is 500 pM.

4. A method of diagnosing whether a subject suffers from a combination of two or more liver pathologies selected from hepatitis C, cirrhosis, and liver cancer comprising the steps of:
   (a) identifying, using a first anti-hPG antibody, whether said subject previously diagnosed with at least one liver pathology selected from hepatitis C, cirrhosis, and liver cancer has a serum or plasma human progastrin (hPG) concentration above a threshold value, where the threshold value is at least about 400 pM, and
   (b) testing said patient for at least one other liver pathology selected from liver cancer, hepatitis C and cirrhosis,
   thereby diagnosing whether the subject suffers from at least two liver pathologies selected from liver cancer, hepatitis C and cirrhosis.

5. The method of claim 4, in which the threshold value is 400 pM.

6. The method of claim 4, in which the threshold value is 500 pM.

7. The method of claim 4, further comprising using a second antibody specific for a different epitope of hPG than the first antibody and determining the concentration of hPG based upon the amount of hPG bound by both antibodies.

8. The method of claim 7, wherein at least one of said antibodies is coupled to a detectable marker.

9. The method of any one of claims 4, 5, and 7, wherein said first anti-hPG antibody is a monoclonal antibody.

10. The method of claim 9, wherein said first anti-hPG antibody binds a C-terminal epitope of hPG.

11. The method of claim 9, wherein said first anti-hPG antibody binds an N-terminal epitope of hPG.

12. A method of diagnosing whether a subject suffers from a combination of liver cancer and at least one other liver pathology selected from hepatitis C and cirrhosis comprising the step of:
    identifying, using a first anti-hPG antibody, whether said subject has a serum or plasma hPG concentration above a threshold value, where the threshold value is at least about 100 pM, wherein a serum concentration above the threshold value indicates that the subject suffers from a combination of liver cancer and at least one other liver pathology selected from hepatitis C and cirrhosis, and
    wherein said anti-hPG antibody has a light chain CDR1 domain comprising the amino acid sequence of SEQ ID NO: 50, a light chain CDR2 domain comprising the amino acid sequence of SEQ ID NO: 53, a light chain CDR3 domain comprising the amino acid sequence of SEQ ID NO: 57, a heavy chain CDR1 domain comprising the amino acid sequence of SEQ ID NO: 39, a heavy chain CDR2 domain comprising the amino acid sequence of SEQ ID NO: 43, and a heavy chain CDR3 domain comprising the amino acid sequence of SEQ ID NO: 47.

13. A method of diagnosing whether a subject suffers from a combination of two or more liver pathologies selected from hepatitis C, cirrhosis, and liver cancer comprising the step of:
    identifying, using a first anti-hPG antibody, whether said subject has a serum or plasma hPG concentration above a threshold value, where the threshold value is at least about 400 pM, wherein a serum concentration above the threshold indicates that the subject suffers from a combination of two or more liver pathologies selected from hepatitis C, cirrhosis, and liver cancer, and
    wherein said anti-hPG antibody has a light chain CDR1 domain comprising the amino acid sequence of SEQ ID NO: 50, a light chain CDR2 domain comprising the amino acid sequence of SEQ ID NO: 53, a light chain CDR3 domain comprising the amino acid sequence of SEQ ID NO: 57, a heavy chain CDR1 domain comprising the amino acid sequence of SEQ ID NO: 39, a heavy chain CDR2 domain comprising the amino acid sequence of SEQ ID NO: 43, and a heavy chain CDR3 domain comprising the amino acid sequence of SEQ ID NO: 47.

14. The method of claim 12 or 13, wherein said anti-hPG antibody is a Fab', F(ab')$_2$, Fv, rIgG, or scFv.

15. The method of claim 12 or 13, wherein said anti-hPG antibody is an IgA$_1$, IgA$_2$, IgD, IgE, IgG$_1$, IgG$_2$, IgG$_3$, IgG$_4$, or IgM.

16. The method of claim 15, wherein said anti-hPG antibody is an IgG$_1$.

17. The method of claim 12 or 13, wherein said anti-hPG antibody is a monoclonal antibody.

18. The method of claim 17, wherein said monoclonal anti-hPG antibody is a mouse monoclonal antibody.

19. The method of claim 18, wherein said mouse monoclonal anti-hPG antibody has a light chain variable region comprising the amino acid sequence of SEQ ID NO: 65 and a heavy chain variable region comprising the amino acid sequence of SEQ ID NO: 61.

20. The method of claim 17, wherein said monoclonal anti-hPG antibody is a humanized monoclonal anti-hPG antibody.

21. The method of claim 20, wherein said first anti-hPG antibody has a light chain variable region comprising the amino acid sequence of SEQ ID NO: 85 and a heavy chain variable region comprising the amino acid sequence of SEQ ID NO: 84.

22. The method of claim 20, wherein said first anti-hPG antibody has a light chain variable region comprising the amino acid sequence of SEQ ID NO: 87 and a heavy chain variable region comprising the amino acid sequence of SEQ ID NO: 86.

23. The method of claim 20, wherein said first anti-hPG antibody has a light chain variable region comprising the amino acid sequence of SEQ ID NO: 89 and a heavy chain variable region comprising the amino acid sequence of SEQ ID NO: 88.

24. The method of claim 12 or 13, further comprising using a second antibody specific for a different epitope of hPG than the first antibody and determining the concentration of hPG based upon the amount of hPG bound by both antibodies.

25. The method of claim 12 or 13, wherein said antibody is coupled to a detectable marker.

26. The method of claim 24, wherein at least one of said antibodies is coupled to a detectable marker.

27. The method of claim 24, wherein said second anti-hPG antibody binds a C-terminal epitope of hPG.

28. The method of claim 26, wherein said detectable marker is horseradish peroxidase, alkaline phosphatase, beta-galactosidase, or acetylcholinesterase.

29. The method of claim 26, wherein said detectable marker is umbelliferone, fluorescein, fluorescein isothiocyanate, rhodamine, dichlorotriazinylamine fluroescein, dansyl chloride, or phycoerythrin.

30. The method of claim 26, wherein said detectable marker is luminol, luciferase, luciferin, or aequorin.

31. The method of claim 26, wherein said detectable marker is $^{125}$I, $^{131}$I, $^{111}$In, or $^{99}$Tc.

* * * * *

SEQUENCE LISTING

```
<160> NUMBER OF SEQ ID NOS: 106

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Ile Phe Thr Ser Tyr Trp
1               5

<210> SEQ ID NO 2
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Phe Tyr Pro Gly Asn Ser Asp Ser
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Thr Arg Arg Asp Ser Pro Gln Tyr
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Ser Ile Val His Ser Asn Gly Asn Thr Tyr
1               5                   10

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Val Ser
1

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Phe Gln Gly Ser His Val Pro Phe Thr
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Tyr Thr Phe Ser Ser Ser Trp
```

```
<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Phe Leu Pro Gly Ser Gly Ser Thr
1               5

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Thr Asp Gly Asn Tyr Asp Trp Phe Ala Tyr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Ser Leu Val His Ser Ser Gly Val Thr Tyr
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Gln Ser Thr His Val Pro Pro Thr
1               5

<210> SEQ ID NO 12
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Ile Phe Thr Ser Tyr
                20                  25                  30

Trp Val His Trp Val Lys Gln Arg Pro Gly Gln Gly Leu Glu Trp Ile
            35                  40                  45

Gly Gly Phe Tyr Pro Gly Asn Ser Asp Ser Arg Tyr Asn Gln Lys Phe
```

```
            50                  55                  60
Lys Gly Lys Ala Thr Leu Thr Ala Val Thr Ser Ala Ser Thr Ala Tyr
 65                  70                  75                  80

Met Asp Leu Ser Ser Leu Thr Asn Glu Asp Ser Ala Val Tyr Phe Cys
                 85                  90                  95

Thr Arg Arg Asp Ser Pro Gln Tyr Trp Gly Gln Gly Thr Thr Leu Thr
                100                 105                 110

Val Ser Ser
        115

<210> SEQ ID NO 13
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Val Leu Met Thr Gln Thr Pro Leu Ser Leu Pro Val Ser Leu Gly
  1               5                  10                  15

Asp Gln Ala Ser Ile Ser Cys Arg Ser Ser Gln Ser Ile Val His Ser
             20                  25                  30

Asn Gly Asn Thr Tyr Leu Glu Trp Tyr Leu Gln Lys Pro Gly Gln Ser
         35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Leu Glu Ala Glu Asp Leu Gly Val Tyr Tyr Cys Phe Gln Gly
                 85                  90                  95

Ser His Val Pro Phe Thr Phe Gly Gly Gly Thr Lys Leu Glu Ile Lys
                100                 105                 110

<210> SEQ ID NO 14
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Gln Gln Ser Gly Ala Glu Leu Met Lys Pro Gly Ala
  1               5                  10                  15

Ser Val Lys Ile Ser Cys Lys Ala Thr Gly Tyr Thr Phe Ser Ser Ser
             20                  25                  30

Trp Ile Glu Trp Leu Lys Gln Arg Pro Gly His Gly Leu Glu Trp Ile
         35                  40                  45

Gly Glu Phe Leu Pro Gly Ser Gly Ser Thr Asp Tyr Asn Glu Lys Phe
     50                  55                  60

Lys Gly Lys Ala Thr Phe Thr Ala Asp Thr Ser Ser Asp Thr Ala Tyr
 65                  70                  75                  80

Met Leu Leu Ser Ser Leu Thr Ser Glu Asp Ser Ala Val Tyr Tyr Cys
                 85                  90                  95

Ala Thr Asp Gly Asn Tyr Asp Trp Phe Ala Tyr Trp Gly Gln Gly Thr
                100                 105                 110

Leu Val Thr Val Ser Ala
```

<210> SEQ ID NO 15
<211> LENGTH: 112
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 15

Asp Leu Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Ser Gly Val Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Ser Gly Thr Lys Leu Glu Ile Lys
            100                 105                 110

<210> SEQ ID NO 16
<211> LENGTH: 345
<212> TYPE: DNA
<213> ORGANISM: Artificial Sequence
<220> FEATURE:
<223> OTHER INFORMATION: Description of Artificial Sequence: Synthetic
       polynucleotide
<220> FEATURE:
<221> NAME/KEY: CDS
<222> LOCATION: (1)..(345)

<400> SEQUENCE: 16 gag gtt cag ctc cag cag tct ggg act gtg ctg gca agg cct ggg gct      48
Glu Val Gln Leu Gln Gln Ser Gly Thr Val Leu Ala Arg Pro Gly Ala
1               5                   10                  15 tcc gtg aag atg tcc tgc aag gct tct ggc tac atc ttt acc agc tac      96
Ser Val Lys Met Ser Cys Lys Ala Ser Gly Tyr Ile Phe Thr Ser Tyr
            20                  25                  30 tgg gta cac tgg gtt aaa cag agg cct gga cag ggt cta gaa tgg att     144
Trp Val His Trp Val Lys Gln Arg Pro Gly Gln Gly Leu Glu Trp Ile
        35                  40                  45 ggt ggt ttt tat cct gga aat agt gat tct agg tac aac cag aaa ttc     192
Gly Gly Phe Tyr Pro Gly Asn Ser Asp Ser Arg Tyr Asn Gln Lys Phe
    50                  55                  60 aag ggc aag gcc aca ctg act gca gtc aca tcc gcc agt act gcc tac     240
Lys Gly Lys Ala Thr Leu Thr Ala Val Thr Ser Ala Ser Thr Ala Tyr
65                  70                  75                  80 atg gac ctc agc agc ctg aca aat gag gac tct gcg gtc tat ttc tgt     288
Met Asp Leu Ser Ser Leu Thr Asn Glu Asp Ser Ala Val Tyr Phe Cys
                85                  90                  95 aca aga aga gat agt ccc cag tac tgg ggc caa ggc acc act ctc aca     336
Thr Arg Arg Asp Ser Pro Gln Tyr Trp Gly Gln Gly Thr Thr Leu Thr
            100                 105                 110 gtc tcc tca                                                          345
Val Ser Ser
        115

<210> SEQ ID NO 17
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 17

```
gat gtt ttg atg acc caa act cca ctc tcc ctg cct gtc agt ctt gga        48
Asp Val Leu Met Thr Gln Thr Pro Leu Ser Leu Pro Val Ser Leu Gly
1               5                   10                  15 gat caa gcc tcc atc tct tgc aga tct agt cag agc att gta cat agt        96
Asp Gln Ala Ser Ile Ser Cys Arg Ser Ser Gln Ser Ile Val His Ser
            20                  25                  30 aat gga aac acc tat tta gaa tgg tac ctg cag aaa cca ggc cag tct       144
Asn Gly Asn Thr Tyr Leu Glu Trp Tyr Leu Gln Lys Pro Gly Gln Ser
        35                  40                  45 cca aag ctc ctg atc tac aaa gtt tcc aac cga ttt tct ggg gtc cca       192
Pro Lys Leu Leu Ile Tyr Lys Val Ser Asn Arg Phe Ser Gly Val Pro
    50                  55                  60 gac agg ttc agt ggc agt gga tca ggg aca gat ttc aca ctc aag atc       240
Asp Arg Phe Ser Gly Ser Gly Ser Gly Thr Asp Phe Thr Leu Lys Ile
65                  70                  75                  80 agc aga ctg gag gct gag gat ctg gga gtt tat tac tgc ttt caa ggt       288
Ser Arg Leu Glu Ala Glu Asp Leu Gly Val Tyr Tyr Cys Phe Gln Gly
                85                  90                  95 tca cat gtt ccg ttc acg ttc gga ggg ggg acc aag ctg gaa ata aaa       336
Ser His Val Pro Phe Thr Phe Gly Gly Gly Thr Lys Leu Glu Ile Lys
            100                 105                 110
```

<210> SEQ ID NO 18
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(354)

<400> SEQUENCE: 18

```
cag gtt cag ttg cag cag tct gga gct gag ctg atg aag cca ggg gcc        48
Gln Val Gln Leu Gln Gln Ser Gly Ala Glu Leu Met Lys Pro Gly Ala
1               5                   10                  15 tca gtg aag ata tcc tgc aag gct act ggc tac aca ttc agt agc tcc        96
Ser Val Lys Ile Ser Cys Lys Ala Thr Gly Tyr Thr Phe Ser Ser Ser
            20                  25                  30 tgg ata gag tgg tta aaa cag agg cct gga cat ggc ctt gag tgg att       144
Trp Ile Glu Trp Leu Lys Gln Arg Pro Gly His Gly Leu Glu Trp Ile
        35                  40                  45 gga gag ttt tta cct gga agt ggt agt aca gac tac aat gag aag ttc       192
Gly Glu Phe Leu Pro Gly Ser Gly Ser Thr Asp Tyr Asn Glu Lys Phe
    50                  55                  60 aag ggc aag gcc aca ttc act gca gac aca tcc tcc gac aca gcc tac       240
Lys Gly Lys Ala Thr Phe Thr Ala Asp Thr Ser Ser Asp Thr Ala Tyr
65                  70                  75                  80 atg cta ctc agc agc ctg aca tct gag gac tct gcc gtc tat tac tgt       288
Met Leu Leu Ser Ser Leu Thr Ser Glu Asp Ser Ala Val Tyr Tyr Cys
```

```
                        85                  90                  95
gca act gat ggt aat tat gac tgg ttt gct tac tgg ggc caa ggg act         336
Ala Thr Asp Gly Asn Tyr Asp Trp Phe Ala Tyr Trp Gly Gln Gly Thr
                100                 105                 110 ctg gtc act gtc tct gca                                                 354
Leu Val Thr Val Ser Ala
        115

<210> SEQ ID NO 19
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 19 gat ctt gtg atg acc caa act cca ctc tcc ctg cct gtc agt ctt gga         48
Asp Leu Val Met Thr Gln Thr Pro Leu Ser Leu Pro Val Ser Leu Gly
1               5                   10                  15 gat caa gcc tcc atc tct tgc aga tct agt cag agc ctt gta cac agt         96
Asp Gln Ala Ser Ile Ser Cys Arg Ser Ser Gln Ser Leu Val His Ser
            20                  25                  30 agt gga gtc acc tat tta cat tgg tac ctg cag aag cca ggc cag tct         144
Ser Gly Val Thr Tyr Leu His Trp Tyr Leu Gln Lys Pro Gly Gln Ser
        35                  40                  45 cca aag ctc ctg atc tac aaa gtt tcc aac cga ttt tct ggg gtc cca         192
Pro Lys Leu Leu Ile Tyr Lys Val Ser Asn Arg Phe Ser Gly Val Pro
    50                  55                  60 gac agg ttc agt ggc agt gga tca ggg aca gat ttc aca ctc aag atc         240
Asp Arg Phe Ser Gly Ser Gly Ser Gly Thr Asp Phe Thr Leu Lys Ile
65                  70                  75                  80 agc aga gtg gag gct gag gat ctg gga gtt tat ttc tgc tct caa agt         288
Ser Arg Val Glu Ala Glu Asp Leu Gly Val Tyr Phe Cys Ser Gln Ser
                85                  90                  95 aca cat gtt cct ccc acg ttc ggc tcg ggg aca aag ttg gaa ata aaa         336
Thr His Val Pro Pro Thr Phe Gly Ser Gly Thr Lys Leu Glu Ile Lys
            100                 105                 110

<210> SEQ ID NO 20
<211> LENGTH: 80
<212> TYPE: PRT
<213> ORGANISM: Homo sapiens

<400> SEQUENCE: 20

Ser Trp Lys Pro Arg Ser Gln Gln Pro Asp Ala Pro Leu Gly Thr Gly
1               5                   10                  15

Ala Asn Arg Asp Leu Glu Leu Pro Trp Leu Glu Gln Gln Gly Pro Ala
            20                  25                  30

Ser His His Arg Arg Gln Leu Gly Pro Gln Gly Pro Pro His Leu Val
        35                  40                  45

Ala Asp Pro Ser Lys Lys Gln Gly Pro Trp Leu Glu Glu Glu Glu Glu
    50                  55                  60

Ala Tyr Gly Trp Met Asp Phe Gly Arg Arg Ser Ala Glu Asp Glu Asn
65                  70                  75                  80

<210> SEQ ID NO 21
<211> LENGTH: 115
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Tyr
                20                  25                  30

Trp Val His Trp Val Arg Gln Ala Pro Gly Gln Arg Leu Glu Trp Met
            35                  40                  45

Gly Gly Phe Tyr Pro Gly Asn Ser Asp Ser Arg Tyr Ser Gln Lys Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Arg Asp Ser Pro Gln Tyr Trp Gly Gln Gly Thr Leu Val Thr
                100                 105                 110

Val Ser Ser
        115

<210> SEQ ID NO 22
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
                20                  25                  30

Asn Gly Asn Thr Tyr Leu Glu Trp Phe Gln Gln Arg Pro Gly Gln Ser
            35                  40                  45

Pro Arg Arg Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gly Gly Thr Lys Val Glu Ile Lys
                100                 105                 110

<210> SEQ ID NO 23
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Ser
                20                  25                  30

Trp Met His Trp Val Arg Gln Ala Pro Gly Gln Gly Leu Glu Trp Met
        35                  40                  45

Gly Ile Phe Leu Pro Gly Ser Gly Ser Thr Asp Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Asp Gly Asn Tyr Asp Trp Phe Ala Tyr Trp Gly Gln Gly Thr
            100                 105                 110

Leu Val Thr Val Ser Ser
        115

<210> SEQ ID NO 24
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Ser
            20                  25                  30

Ser Gly Val Thr Tyr Leu Tyr Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Pro Thr Phe Gly Gln Gly Thr Lys Leu Glu Ile Lys
            100                 105                 110

<210> SEQ ID NO 25
<211> LENGTH: 14
<212> TYPE: PRT
<213> ORGANISM: Homo sapiens

<400> SEQUENCE: 25

Ser Trp Lys Pro Arg Ser Gln Gln Pro Asp Ala Pro Leu Gly
1               5                   10

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Ahx

<400> SEQUENCE: 26

Ser Trp Lys Pro Arg Ser Gln Gln Pro Asp Ala Pro Leu Gly Xaa Cys
1               5                   10                  15

```
<210> SEQ ID NO 27
<211> LENGTH: 26
<212> TYPE: PRT
<213> ORGANISM: Homo sapiens

<400> SEQUENCE: 27

Gln Gly Pro Trp Leu Glu Glu Glu Glu Ala Tyr Gly Trp Met Asp
1               5                   10                  15

Phe Gly Arg Arg Ser Ala Glu Asp Glu Asn
            20                  25

<210> SEQ ID NO 28
<211> LENGTH: 5
<212> TYPE: PRT
<213> ORGANISM: Homo sapiens

<400> SEQUENCE: 28

Asp Ala Pro Leu Gly
1               5

<210> SEQ ID NO 29
<211> LENGTH: 6
<212> TYPE: PRT
<213> ORGANISM: Homo sapiens

<400> SEQUENCE: 29

Pro Asp Ala Pro Leu Gly
1               5

<210> SEQ ID NO 30
<211> LENGTH: 7
<212> TYPE: PRT
<213> ORGANISM: Homo sapiens

<400> SEQUENCE: 30

Pro Arg Ser Gln Gln Pro Asp
1               5

<210> SEQ ID NO 31
<211> LENGTH: 9
<212> TYPE: PRT
<213> ORGANISM: Homo sapiens

<400> SEQUENCE: 31

Trp Lys Pro Arg Ser Gln Gln Pro Asp
1               5

<210> SEQ ID NO 32
<211> LENGTH: 13
<212> TYPE: PRT
<213> ORGANISM: Homo sapiens

<400> SEQUENCE: 32

Trp Lys Pro Arg Ser Gln Gln Pro Asp Ala Pro Leu Gly
1               5                   10

<210> SEQ ID NO 33
<211> LENGTH: 4
<212> TYPE: PRT
<213> ORGANISM: Homo sapiens

<400> SEQUENCE: 33

Phe Gly Arg Arg
```

```
<210> SEQ ID NO 34
<211> LENGTH: 5
<212> TYPE: PRT
<213> ORGANISM: Homo sapiens

<400> SEQUENCE: 34

Met Asp Phe Gly Arg
1               5

<210> SEQ ID NO 35
<211> LENGTH: 5
<212> TYPE: PRT
<213> ORGANISM: Homo sapiens

<400> SEQUENCE: 35

Ala Glu Asp Glu Asn
1               5

<210> SEQ ID NO 36
<211> LENGTH: 8
<212> TYPE: PRT
<213> ORGANISM: Homo sapiens

<400> SEQUENCE: 36

Gly Trp Met Asp Phe Gly Arg Arg
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Phe Thr Phe Thr Thr Tyr Ala
1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Phe Ile Phe Ser Ser Tyr Gly
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Tyr Thr Phe Thr Ser Tyr Tyr
1               5

<210> SEQ ID NO 40
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Tyr Ser Ile Thr Ser Asp Tyr Ala
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ile Ser Ser Gly Gly Thr Tyr Thr
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ile Asn Thr Phe Gly Asp Arg Thr
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ile Asn Pro Ser Asn Gly Gly Thr
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ile Ser Phe Ser Gly Tyr Thr
1               5

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45
```

```
Ala Thr Gln Gly Asn Tyr Ser Leu Asp Phe
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Arg Gly Thr Gly Thr Tyr
1               5

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Thr Arg Gly Gly Tyr Tyr Pro Phe Asp Tyr
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ala Arg Glu Val Asn Tyr Gly Asp Ser Tyr His Phe Asp Tyr
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Lys Ser Leu Arg His Thr Lys Gly Ile Thr Phe
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Ser Leu Leu Asp Ser Asp Gly Lys Thr Tyr
1               5                   10

<210> SEQ ID NO 51
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 51

Ser Gln His Arg Thr Tyr Thr
1               5

<210> SEQ ID NO 52
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Met Ser
1

<210> SEQ ID NO 53
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Leu Val Ser
1

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Val Lys Lys Asp Gly Ser His
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Gln Asn Leu Glu Leu Pro Leu Thr
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Trp Gln Gly Thr His Phe Pro Gln Thr
1               5
```

```
<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Trp Gln Gly Thr His Ser Pro Tyr Thr
1               5

<210> SEQ ID NO 58
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Val Gly Asp Ala Ile Lys Gly Gln Ser Val Phe Val
1               5                   10

<210> SEQ ID NO 59
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Thr Thr Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Thr Tyr Thr Tyr Tyr Pro Asp Ser Val
    50                  55                  60

Lys Gly Arg Phe Thr Ile Ser Arg Asp Asn Ala Lys Asn Ala Leu Tyr
65                  70                  75                  80

Leu Gln Met Ser Ser Leu Arg Ser Glu Asp Thr Ala Met Tyr Tyr Cys
                85                  90                  95

Ala Thr Gln Gly Asn Tyr Ser Leu Asp Phe Trp Gly Gln Gly Thr Ser
            100                 105                 110

Leu Thr Val Ser Ser
        115

<210> SEQ ID NO 60
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ile Phe Ser Ser Tyr
            20                  25                  30
```

Gly Met Ser Trp Val Arg Gln Ser Pro Asp Arg Arg Leu Glu Leu Val
            35                  40                  45

Ala Ser Ile Asn Thr Phe Gly Asp Arg Thr Tyr Tyr Pro Asp Ser Val
 50                  55                  60

Lys Gly Arg Phe Thr Ile Ser Arg Asp Asn Ala Lys Asn Thr Leu Tyr
 65                  70                  75                  80

Leu Gln Met Thr Ser Leu Lys Ser Glu Asp Thr Ala Ile Tyr Tyr Cys
                 85                  90                  95

Ala Arg Gly Thr Gly Thr Tyr Trp Gly Gln Gly Thr Leu Thr Val
                100                 105                 110

Ser Ser

<210> SEQ ID NO 61
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Gln Gln Ser Gly Ala Glu Leu Val Lys Pro Gly Ala
 1               5                   10                  15

Ser Val Lys Leu Ser Cys Lys Ala Ser Gly Tyr Thr Phe Thr Ser Tyr
                 20                  25                  30

Tyr Met Tyr Trp Val Lys Gln Arg Pro Gly Gln Gly Leu Glu Trp Ile
             35                  40                  45

Gly Glu Ile Asn Pro Ser Asn Gly Gly Thr Asn Phe Asn Glu Lys Phe
 50                  55                  60

Lys Ser Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Thr Arg Gly Gly Tyr Tyr Pro Phe Asp Tyr Trp Gly Gln Gly Thr Thr
                100                 105                 110

Leu Thr Val Ser Ser
            115

<210> SEQ ID NO 62
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Asp Val Gln Leu Gln Glu Ser Gly Pro Gly Leu Val Lys Pro Ser Gln
 1               5                   10                  15

Ser Leu Ser Leu Thr Cys Thr Val Thr Gly Tyr Ser Ile Thr Ser Asp
                 20                  25                  30

Tyr Ala Trp Asn Trp Ile Arg Gln Phe Pro Gly Asn Lys Leu Glu Trp
             35                  40                  45

Met Gly Tyr Ile Ser Phe Ser Gly Tyr Thr Ser Tyr Asn Pro Ser Leu
             50                  55                  60

Lys Ser Arg Ile Ser Val Thr Arg Asp Thr Ser Arg Asn Gln Phe Phe
 65                  70                  75                  80

Leu Gln Leu Thr Ser Val Thr Thr Glu Asp Thr Ala Thr Tyr Tyr Cys

```
                    85                  90                  95

Ala Arg Glu Val Asn Tyr Gly Asp Ser Tyr His Phe Asp Tyr Trp Gly
                100                 105                 110

Gln Gly Thr Ile Val Thr Val Ser Ser
            115                 120

<210> SEQ ID NO 63
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Asp Ile Val Met Thr Gln Ala Ala Ser Ser Asn Pro Val Thr Leu Gly
1               5                   10                  15

Thr Ser Ala Ser Ile Ser Cys Arg Ser Ser Lys Ser Leu Arg His Thr
            20                  25                  30

Lys Gly Ile Thr Phe Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Leu Gly Val Tyr Tyr Cys Ala Gln Asn
                85                  90                  95

Leu Glu Leu Pro Leu Thr Phe Gly Ala Gly Thr Lys Leu Glu Leu Lys
                100                 105                 110

<210> SEQ ID NO 64
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Asp Val Val Leu Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
                100                 105                 110

<210> SEQ ID NO 65
<211> LENGTH: 112
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 65

Asp Val Val Met Thr Gln Thr Pro Leu Thr Leu Ser Val Thr Ile Gly
1               5                   10                  15

Arg Pro Ala Ser Ile Ser Cys Lys Ser Ser Gln Ser Leu Leu Asp Ser
            20                  25                  30

Asp Gly Lys Thr Tyr Leu Tyr Trp Leu Leu Gln Arg Pro Gly Gln Ser
        35                  40                  45

Pro Lys Arg Leu Ile Tyr Leu Val Ser Glu Leu Asp Ser Gly Val Pro
    50                  55                  60

Asp Arg Ile Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Ser Pro Tyr Thr Phe Gly Gly Gly Thr Lys Leu Glu Ile Lys
            100                 105                 110

<210> SEQ ID NO 66
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Leu Ala Leu Thr Gln Ser Ser Ser Ala Ser Phe Ser Leu Gly Ala
1               5                   10                  15

Ser Ala Lys Leu Thr Cys Thr Leu Ser Ser Gln His Arg Thr Tyr Thr
            20                  25                  30

Ile Glu Trp Tyr Gln Gln Gln Ser Leu Lys Pro Pro Lys Tyr Val Met
        35                  40                  45

Glu Val Lys Lys Asp Gly Ser His Ser Thr Gly His Gly Ile Pro Asp
    50                  55                  60

Arg Phe Ser Gly Ser Ser Ser Gly Ala Asp Arg Tyr Leu Ser Ile Ser
65                  70                  75                  80

Asn Ile Gln Pro Glu Asp Glu Ala Ile Tyr Ile Cys Gly Val Gly Asp
                85                  90                  95

Ala Ile Lys Gly Gln Ser Val Phe Val Phe Gly Gly Gly Thr Lys Val
            100                 105                 110

Thr Val Leu
        115

<210> SEQ ID NO 67
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(351)

<400> SEQUENCE: 67 gaa gtg cag ctg gtg gag tct ggg gga ggc tta gtg aag cct gga ggg     48
Glu Val Gln Leu Val Glu Ser Gly Gly Gly Leu Val Lys Pro Gly Gly
1               5                   10                  15 tcc ctg aaa ctc tcc tgt gca gcc tct gga ttc act ttc act acc tat     96

```
Ser Leu Lys Leu Ser Cys Ala Ala Ser Gly Phe Thr Phe Thr Thr Tyr
        20                  25                  30 gcc atg tct tgg gtt cgc cag act ccg gag aag agg ctg gag tgg gtc     144
Ala Met Ser Trp Val Arg Gln Thr Pro Glu Lys Arg Leu Glu Trp Val
            35                  40                  45 gca acc att agt agt ggt ggt act tac acc tac tat cca gac agt gtg     192
Ala Thr Ile Ser Ser Gly Gly Thr Tyr Thr Tyr Tyr Pro Asp Ser Val
50                  55                  60 aag ggt cga ttc acc atc tcc aga gac aat gcc aag aac gcc cta tac     240
Lys Gly Arg Phe Thr Ile Ser Arg Asp Asn Ala Lys Asn Ala Leu Tyr
65                  70                  75                  80 ctg caa atg agc agt ctg agg tct gag gac acg gcc atg tat tac tgt     288
Leu Gln Met Ser Ser Leu Arg Ser Glu Asp Thr Ala Met Tyr Tyr Cys
                85                  90                  95 gca aca cag ggg aat tac tct ttg gac ttc tgg ggc caa ggc acc tct     336
Ala Thr Gln Gly Asn Tyr Ser Leu Asp Phe Trp Gly Gln Gly Thr Ser
            100                 105                 110 ctc aca gtc tcc tca                                                 351
Leu Thr Val Ser Ser
            115

<210> SEQ ID NO 68
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(342)

<400> SEQUENCE: 68 gag gtg cag ctg gtg gag tct ggg gga ggc ttg gtg cag cct gga ggg      48
Glu Val Gln Leu Val Glu Ser Gly Gly Gly Leu Val Gln Pro Gly Gly
1               5                   10                  15 tcc ctg aaa ctc tcc tgt gca gcc tct gga ttc att ttc agt agc tat      96
Ser Leu Lys Leu Ser Cys Ala Ala Ser Gly Phe Ile Phe Ser Ser Tyr
            20                  25                  30 ggc atg tct tgg gtt cgc cag tct cca gac agg agg ctg gag ttg gtc     144
Gly Met Ser Trp Val Arg Gln Ser Pro Asp Arg Arg Leu Glu Leu Val
        35                  40                  45 gca agt att aat act ttt ggt gat aga acc tat tat cca gac agt gtg     192
Ala Ser Ile Asn Thr Phe Gly Asp Arg Thr Tyr Tyr Pro Asp Ser Val
50                  55                  60 aag ggc cga ttc acc atc tcc aga gac aat gcc aag aac acc ctg tac     240
Lys Gly Arg Phe Thr Ile Ser Arg Asp Asn Ala Lys Asn Thr Leu Tyr
65                  70                  75                  80 ctg caa atg acc agt ctg aag tct gag gac aca gcc att tat tac tgt     288
Leu Gln Met Thr Ser Leu Lys Ser Glu Asp Thr Ala Ile Tyr Tyr Cys
                85                  90                  95 gca aga ggg acc gga acc tac tgg ggc caa ggc acc act ctc aca gtc     336
Ala Arg Gly Thr Gly Thr Tyr Trp Gly Gln Gly Thr Thr Leu Thr Val
            100                 105                 110 tcc tca                                                             342
Ser Ser

<210> SEQ ID NO 69
<211> LENGTH: 351
<212> TYPE: DNA
<213> ORGANISM: Artificial Sequence
<220> FEATURE:
<223> OTHER INFORMATION: Description of Artificial Sequence: Synthetic
```

```
                      polynucleotide
<220> FEATURE:
<221> NAME/KEY: CDS
<222> LOCATION: (1)..(351)

<400> SEQUENCE: 69 cag gtc caa ctg cag cag tct ggg gct gaa ctg gtg aag cct ggg gct        48
Gln Val Gln Leu Gln Gln Ser Gly Ala Glu Leu Val Lys Pro Gly Ala
1               5                   10                  15 tca gtg aag ttg tcc tgc aag gct tct ggc tac acc ttc acc agc tac        96
Ser Val Lys Leu Ser Cys Lys Ala Ser Gly Tyr Thr Phe Thr Ser Tyr
            20                  25                  30 tat atg tac tgg gtg aag cag agg cct gga caa ggc ctt gag tgg att       144
Tyr Met Tyr Trp Val Lys Gln Arg Pro Gly Gln Gly Leu Glu Trp Ile
        35                  40                  45 gga gag att aat cct agc aat ggt ggt act aac ttc aat gag aag ttc       192
Gly Glu Ile Asn Pro Ser Asn Gly Gly Thr Asn Phe Asn Glu Lys Phe
    50                  55                  60 aag agc aag gcc aca ctg act gta gac aaa tcc tcc agc aca gca tac       240
Lys Ser Lys Ala Thr Leu Thr Val Asp Lys Ser Ser Ser Thr Ala Tyr
65                  70                  75                  80 atg caa ctc agc agc ctg aca tct gag gac tct gcg gtc tat tac tgt       288
Met Gln Leu Ser Ser Leu Thr Ser Glu Asp Ser Ala Val Tyr Tyr Cys
                85                  90                  95 aca aga ggc ggt tac tac ccc ttt gac tac tgg ggc caa ggc acc act       336
Thr Arg Gly Gly Tyr Tyr Pro Phe Asp Tyr Trp Gly Gln Gly Thr Thr
            100                 105                 110 ctc aca gtc tcc tca                                                    351
Leu Thr Val Ser Ser
        115

<210> SEQ ID NO 70
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(363)

<400> SEQUENCE: 70 gat gtg cag ctt cag gag tcg gga cct ggc ctg gtg aaa cct tct cag        48
Asp Val Gln Leu Gln Glu Ser Gly Pro Gly Leu Val Lys Pro Ser Gln
1               5                   10                  15 tct ctg tcc ctc aca tgc act gtc act ggc tac tca atc acc agt gat        96
Ser Leu Ser Leu Thr Cys Thr Val Thr Gly Tyr Ser Ile Thr Ser Asp
            20                  25                  30 tat gcc tgg aat tgg atc cgg cag ttt cca gga aac aaa ctg gag tgg       144
Tyr Ala Trp Asn Trp Ile Arg Gln Phe Pro Gly Asn Lys Leu Glu Trp
        35                  40                  45 atg ggc tac ata agc ttc agt ggt tac act agt tac aac cca tct ctc       192
Met Gly Tyr Ile Ser Phe Ser Gly Tyr Thr Ser Tyr Asn Pro Ser Leu
    50                  55                  60 aaa agt cga atc tct gtc act cgg gac aca tcc agg aac caa ttc ttc       240
Lys Ser Arg Ile Ser Val Thr Arg Asp Thr Ser Arg Asn Gln Phe Phe
65                  70                  75                  80 ctc cag ttg act tct gtg act act gag gac aca gcc aca tat tac tgt       288
Leu Gln Leu Thr Ser Val Thr Thr Glu Asp Thr Ala Thr Tyr Tyr Cys
                85                  90                  95 gca aga gag gtc aac tat ggg gac tcc tac cac ttt gac tac tgg ggc       336
Ala Arg Glu Val Asn Tyr Gly Asp Ser Tyr His Phe Asp Tyr Trp Gly
```

```
                    100                 105                 110
caa ggc acc att gtc aca gtc tcc tca                                    363
Gln Gly Thr Ile Val Thr Val Ser Ser
        115                 120

<210> SEQ ID NO 71
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 71 gac att gtg atg acg cag gct gca tcc tct aat cca gtc act ctt gga         48
Asp Ile Val Met Thr Gln Ala Ala Ser Ser Asn Pro Val Thr Leu Gly
1               5                   10                  15 aca tcc gct tcc atc tcc tgc agg tct agt aag agt ctc cga cat act         96
Thr Ser Ala Ser Ile Ser Cys Arg Ser Ser Lys Ser Leu Arg His Thr
            20                  25                  30 aaa ggc atc act ttt ttg tat tgg tat ctg cag aag cca ggc cag tct        144
Lys Gly Ile Thr Phe Leu Tyr Trp Tyr Leu Gln Lys Pro Gly Gln Ser
        35                  40                  45 cct cag ctc ctg att tat cag atg tcc aac ctt gcc tca gga gtc cca        192
Pro Gln Leu Leu Ile Tyr Gln Met Ser Asn Leu Ala Ser Gly Val Pro
    50                  55                  60 gac agg ttc agt agc agt ggg tca gga act gat ttc aca ctg aga atc        240
Asp Arg Phe Ser Ser Ser Gly Ser Gly Thr Asp Phe Thr Leu Arg Ile
65                  70                  75                  80 agc aga gtg gag gct gag gat ttg ggt gtt tat tac tgt gct caa aat        288
Ser Arg Val Glu Ala Glu Asp Leu Gly Val Tyr Tyr Cys Ala Gln Asn
                85                  90                  95 cta gaa ctt ccg ctc acg ttc ggt gct ggg acc aag ctg gag ctg aaa        336
Leu Glu Leu Pro Leu Thr Phe Gly Ala Gly Thr Lys Leu Glu Leu Lys
            100                 105                 110

<210> SEQ ID NO 72
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 72 gat gtt gtg ctg acc cag act cca ctc act ttg tcg gtt acc att gga         48
Asp Val Val Leu Thr Gln Thr Pro Leu Thr Leu Ser Val Thr Ile Gly
1               5                   10                  15 caa cca gcc tcc atc tcc tgc aag tca agt cag agc ctc tta gat agt         96
Gln Pro Ala Ser Ile Ser Cys Lys Ser Ser Gln Ser Leu Leu Asp Ser
            20                  25                  30 gat gga aag aca tat ttg aat tgg ttg tta cag agg cca ggc cag tct        144
Asp Gly Lys Thr Tyr Leu Asn Trp Leu Leu Gln Arg Pro Gly Gln Ser
        35                  40                  45 cca aag cgc cta atc tat ctg gtg tct aaa ctg gac tct gga gtc cct        192
Pro Lys Arg Leu Ile Tyr Leu Val Ser Lys Leu Asp Ser Gly Val Pro
    50                  55                  60 gac agg ttc act ggc agt gga tca ggg aca gat ttc aca ctg aaa atc        240
Asp Arg Phe Thr Gly Ser Gly Ser Gly Thr Asp Phe Thr Leu Lys Ile
```

```
Asp Arg Phe Thr Gly Ser Gly Ser Gly Thr Asp Phe Thr Leu Lys Ile
 65                  70                  75                  80 agc aga gtg gag gct gag gat ttg gga gtt tat tat tgc tgg caa ggt    288
Ser Arg Val Glu Ala Glu Asp Leu Gly Val Tyr Tyr Cys Trp Gln Gly
                 85                  90                  95 aca cat ttt cct cag acg ttc ggt gga ggc acc aag ctg gaa atc aaa    336
Thr His Phe Pro Gln Thr Phe Gly Gly Gly Thr Lys Leu Glu Ile Lys
            100                 105                 110
```

<210> SEQ ID NO 73
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 73

```
gat gtt gtg atg acc cag act cca ctc act ttg tcg gtt acc att ggg     48
Asp Val Val Met Thr Gln Thr Pro Leu Thr Leu Ser Val Thr Ile Gly
  1               5                  10                  15 cgc cca gcc tcc atc tct tgc aag tca agt cag agc ctc tta gac agt     96
Arg Pro Ala Ser Ile Ser Cys Lys Ser Ser Gln Ser Leu Leu Asp Ser
                 20                  25                  30 gat gga aag aca tat ttg tat tgg ttg tta cag agg cca ggc cag tct    144
Asp Gly Lys Thr Tyr Leu Tyr Trp Leu Leu Gln Arg Pro Gly Gln Ser
             35                  40                  45 cca aag cgc cta atc tat ctg gtg tct gag ctg gac tct gga gtc cct    192
Pro Lys Arg Leu Ile Tyr Leu Val Ser Glu Leu Asp Ser Gly Val Pro
         50                  55                  60 gac agg atc act ggc agt ggg tcg ggg aca gat ttc aca ctg aag atc    240
Asp Arg Ile Thr Gly Ser Gly Ser Gly Thr Asp Phe Thr Leu Lys Ile
 65                  70                  75                  80 agc aga gtg gag gct gag gat ttg gga gtt tat tat tgc tgg caa gga    288
Ser Arg Val Glu Ala Glu Asp Leu Gly Val Tyr Tyr Cys Trp Gln Gly
                 85                  90                  95 aca cat tct ccg tac acg ttc gga ggg ggg acc aag ctg gaa ata aaa    336
Thr His Ser Pro Tyr Thr Phe Gly Gly Gly Thr Lys Leu Glu Ile Lys
            100                 105                 110
```

<210> SEQ ID NO 74
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(345)

<400> SEQUENCE: 74

```
caa ctt gcg ctc act cag tca tct tca gcc tct ttc tcc ctg gga gcc     48
Gln Leu Ala Leu Thr Gln Ser Ser Ser Ala Ser Phe Ser Leu Gly Ala
  1               5                  10                  15 tca gca aaa cta acg tgc act ttg agt agt caa cac aga acg tac acc     96
Ser Ala Lys Leu Thr Cys Thr Leu Ser Ser Gln His Arg Thr Tyr Thr
                 20                  25                  30 att gaa tgg tat cag caa cag tca ctc aag cct cct aag tat gtg atg    144
Ile Glu Trp Tyr Gln Gln Gln Ser Leu Lys Pro Pro Lys Tyr Val Met
             35                  40                  45
```

| | | | | | | | | | | | | | | | |
|---|---|---|---|---|---|---|---|---|---|---|---|---|---|---|---|
| gag | gtt | aag | aaa | gat | gga | agc | cac | agc | aca | ggt | cat | ggg | att | cct | gat | 192 |
| Glu | Val | Lys | Lys | Asp | Gly | Ser | His | Ser | Thr | Gly | His | Gly | Ile | Pro | Asp | |
| | 50 | | | | 55 | | | | 60 | | | | | | | |

| cgc | ttc | tct | gga | tcc | agt | tct | ggt | gct | gat | cgc | tac | ctc | agc | att | tcc | 240 |
|---|---|---|---|---|---|---|---|---|---|---|---|---|---|---|---|---|
| Arg | Phe | Ser | Gly | Ser | Ser | Ser | Gly | Ala | Asp | Arg | Tyr | Leu | Ser | Ile | Ser | |
| 65 | | | | | 70 | | | | | 75 | | | | | 80 | |

| aac | atc | cag | cct | gaa | gat | gaa | gca | ata | tac | atc | tgt | ggt | gtg | ggt | gat | 288 |
|---|---|---|---|---|---|---|---|---|---|---|---|---|---|---|---|---|
| Asn | Ile | Gln | Pro | Glu | Asp | Glu | Ala | Ile | Tyr | Ile | Cys | Gly | Val | Gly | Asp | |
| | | | | 85 | | | | | 90 | | | | | 95 | | |

| gca | att | aag | gga | caa | tct | gtg | ttt | gtt | ttc | ggc | ggt | ggc | acc | aag | gtc | 336 |
|---|---|---|---|---|---|---|---|---|---|---|---|---|---|---|---|---|
| Ala | Ile | Lys | Gly | Gln | Ser | Val | Phe | Val | Phe | Gly | Gly | Gly | Thr | Lys | Val | |
| | | | 100 | | | | | 105 | | | | | 110 | | | |

| act | gtc | cta | | | | | | | | | | | | | | 345 |
|---|---|---|---|---|---|---|---|---|---|---|---|---|---|---|---|---|
| Thr | Val | Leu | | | | | | | | | | | | | | |
| | | 115 | | | | | | | | | | | | | | |

<210> SEQ ID NO 75
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Ser Trp Val Arg Gln Ala Pro Gly Lys Gly Leu Glu Trp Val
        35                  40                  45

Ser Ser Ile Ser Ser Gly Gly Thr Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
            100                 105                 110

Val Thr Val Ser Ser
        115

<210> SEQ ID NO 76
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Arg His Thr
            20                  25                  30

Lys Gly Ile Thr Phe Leu Tyr Trp Tyr Leu Gln Lys Pro Gly Gln Ser
        35                  40                  45

Pro Gln Leu Leu Ile Tyr Gln Met Ser Asn Arg Ala Ser Gly Val Pro
    50                  55                  60

Asp Arg Phe Ser Gly Ser Gly Ser Gly Thr Asp Phe Thr Leu Lys Ile

```
                        65                  70                  75                  80
Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110

<210> SEQ ID NO 77
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Asn Trp Val Arg Gln Ala Pro Gly Lys Gly Leu Glu Trp Val
        35                  40                  45

Ser Ser Ile Ser Ser Gly Gly Thr Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
            100                 105                 110

Val Thr Val Ser Ser
        115

<210> SEQ ID NO 78
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Arg His Thr
            20                  25                  30

Lys Gly Ile Thr Phe Leu Asp Trp Tyr Leu Gln Lys Pro Gly Gln Ser
        35                  40                  45

Pro Gln Leu Leu Ile Tyr Gln Met Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110

<210> SEQ ID NO 79
<211> LENGTH: 117
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 79

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Ser Trp Val Arg Gln Ala Pro Gly Lys Gly Leu Glu Trp Val
        35                  40                  45

Ser Thr Ile Ser Ser Gly Gly Thr Tyr Thr Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
            100                 105                 110

Val Thr Val Ser Ser
            115

<210> SEQ ID NO 80
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Gly Met Ser Trp Val Arg Gln Ala Pro Gly Lys Gly Leu Glu Trp Val
        35                  40                  45

Ala Asn Ile Asn Thr Phe Gly Asp Arg Thr Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Gly Thr Tyr Trp Gly Gln Gly Thr Leu Val Thr Val
            100                 105                 110

Ser Ser

<210> SEQ ID NO 81
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Asp Val Val Met Thr Gln Ser Pro Leu Ser Leu Pro Val Thr Leu Gly
1               5                   10                  15
```

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gln Thr Phe Gly Gly Gly Thr Lys Val Glu Ile Lys
            100                 105                 110

<210> SEQ ID NO 82
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Gly Met Ser Trp Val Arg Gln Ala Pro Gly Lys Gly Leu Glu Trp Val
        35                  40                  45

Ala Ser Ile Asn Thr Phe Gly Asp Arg Thr Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Gly Thr Tyr Trp Gly Gln Gly Thr Leu Val Thr Val
            100                 105                 110

Ser Ser

<210> SEQ ID NO 83
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Lys Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly

```
                        85                  90                  95
Thr His Phe Pro Gln Thr Phe Gly Gly Gly Thr Lys Val Glu Ile Lys
            100                 105                 110

<210> SEQ ID NO 84
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
        35                  40                  45

Gly Ile Ile Asn Pro Ser Asn Gly Gly Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
            100                 105                 110

Val Thr Val Ser Ser
        115

<210> SEQ ID NO 85
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Tyr Trp Phe Gln Gln Arg Pro Gly Gln Ser
        35                  40                  45

Pro Arg Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Ser Pro Tyr Thr Phe Gly Gln Gly Thr Lys Leu Glu Ile Lys
            100                 105                 110

<210> SEQ ID NO 86
<211> LENGTH: 117
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Asn Gly Gly Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
            100                 105                 110

Val Thr Val Ser Ser
        115

<210> SEQ ID NO 87
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Ser Pro Tyr Thr Phe Gly Gln Gly Thr Lys Leu Glu Ile Lys
            100                 105                 110

<210> SEQ ID NO 88
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
        35                  40                  45

```
Gly Glu Ile Asn Pro Ser Asn Gly Gly Thr Asn Tyr Ala Gln Lys Phe
            50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
            100                 105                 110

Val Thr Val Ser Ser
            115
```

```
<210> SEQ ID NO 89
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Tyr Trp Phe Gln Gln Arg Pro Gly Gln Ser
        35                  40                  45

Pro Arg Arg Leu Ile Tyr Leu Val Ser Glu Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Ser Pro Tyr Thr Phe Gly Gln Gly Thr Lys Leu Glu Ile Lys
            100                 105                 110
```

```
<210> SEQ ID NO 90
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Ile Ser Phe Ser Gly Tyr Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110
```

```
Gln Gly Thr Leu Val Thr Val Ser Ser
        115                 120
```

<210> SEQ ID NO 91
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

```
Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
            20                  25                  30

Ile Glu Trp His Gln Gln Pro Glu Lys Gly Pro Arg Tyr Leu Met
        35                  40                  45

Lys Val Lys Lys Asp Gly Ser His Ser Lys Gly Asp Gly Ile Pro Asp
50                  55                  60

Arg Phe Ser Gly Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
            100                 105                 110

Glu Ile Lys
        115
```

<210> SEQ ID NO 92
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Ser Trp Ile Arg Gln His Pro Gly Lys Gly Leu Glu Trp
        35                  40                  45

Ile Gly Tyr Ile Ser Phe Ser Gly Tyr Thr Tyr Tyr Asn Pro Ser Leu
50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
        115                 120
```

<210> SEQ ID NO 93
<211> LENGTH: 115
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 93

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
            20                  25                  30

Ile Ala Trp His Gln Gln Pro Glu Lys Gly Pro Arg Tyr Leu Met
        35                  40                  45

Lys Val Lys Lys Asp Gly Ser His Ser Lys Gly Asp Gly Ile Pro Asp
50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
                100                 105                 110

Glu Ile Lys
        115

<210> SEQ ID NO 94
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Ile Ser Phe Ser Gly Tyr Thr Ser Tyr Asn Pro Ser Leu
50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
                100                 105                 110

Gln Gly Thr Leu Val Thr Val Ser Ser
        115                 120

<210> SEQ ID NO 95
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gln Leu Val Leu Thr Gln Ser Pro Ser Ala Ser Ala Ser Leu Gly Ala
1               5                   10                  15
```

```
Ser Val Lys Leu Thr Cys Thr Leu Ser Ser Gln His Arg Thr Tyr Thr
             20                  25                  30

Ile Glu Trp His Gln Gln Gln Pro Glu Lys Gly Pro Arg Tyr Leu Met
             35                  40                  45

Glu Val Lys Lys Asp Gly Ser His Ser Lys Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Tyr Cys Gly Val Gly Asp
                 85                  90                  95

Ala Ile Lys Gly Gln Ser Val Phe Val Phe Gly Gly Gly Thr Lys Val
            100                 105                 110

Glu Ile Lys
        115

<210> SEQ ID NO 96
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Ahx

<400> SEQUENCE: 96

Cys Xaa Xaa Gln Gly Pro Trp Leu Glu Glu Glu Glu Ala Tyr Gly
 1               5                  10                  15

Trp Met Asp Phe Gly Arg Arg Ser Ala Glu Asp Glu Asn
             20                  25

<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Ahx

<400> SEQUENCE: 97

Cys Xaa Xaa Phe Gly Arg Arg Ser Ala Glu Asp Glu Asn
 1               5                  10

<210> SEQ ID NO 98
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(12)
<223> OTHER INFORMATION: Ahx

<400> SEQUENCE: 98

Phe Gly Arg Arg Ser Ala Glu Asp Glu Asn Xaa Xaa Cys
 1               5                  10
```

-continued

```
<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Gly Gly Gly Ser Gly Gly Gly Gly Ser Gly Gly Gly Gly Ser
1               5                  10                  15

<210> SEQ ID NO 100
<211> LENGTH: 101
<212> TYPE: PRT
<213> ORGANISM: Homo sapiens

<400> SEQUENCE: 100

Met Gln Arg Leu Cys Val Tyr Val Leu Ile Phe Ala Leu Ala Leu Ala
1               5                  10                  15

Ala Phe Ser Glu Ala Ser Trp Lys Pro Arg Ser Gln Gln Pro Asp Ala
            20                  25                  30

Pro Leu Gly Thr Gly Ala Asn Arg Asp Leu Glu Leu Pro Trp Leu Glu
        35                  40                  45

Gln Gln Gly Pro Ala Ser His His Arg Arg Gln Leu Gly Pro Gln Gly
    50                  55                  60

Pro Pro His Leu Val Ala Asp Pro Ser Lys Lys Gln Gly Pro Trp Leu
65                  70                  75                  80

Glu Glu Glu Glu Glu Ala Tyr Gly Trp Met Asp Phe Gly Arg Arg Ser
                85                  90                  95

Ala Glu Asp Glu Asn
            100

<210> SEQ ID NO 101
<211> LENGTH: 80
<212> TYPE: PRT
<213> ORGANISM: Homo sapiens

<400> SEQUENCE: 101

Ser Trp Lys Pro Arg Ser Gln Gln Pro Asp Ala Pro Leu Gly Thr Gly
1               5                  10                  15

Ala Asn Arg Asp Leu Glu Leu Pro Trp Leu Glu Gln Gln Gly Pro Ala
            20                  25                  30

Ser His His Arg Arg Gln Leu Gly Pro Gln Gly Pro Pro His Leu Val
        35                  40                  45

Ala Asp Pro Ser Lys Lys Gln Gly Pro Trp Leu Glu Glu Glu Glu Glu
    50                  55                  60

Ala Tyr Gly Trp Met Asp Phe Gly Arg Arg Ser Ala Glu Asp Glu Asn
65                  70                  75                  80

<210> SEQ ID NO 102
<211> LENGTH: 34
<212> TYPE: PRT
<213> ORGANISM: Homo sapiens

<400> SEQUENCE: 102

Gln Leu Gly Pro Gln Gly Pro Pro His Leu Val Ala Asp Pro Ser Lys
1               5                  10                  15

Lys Gln Gly Pro Trp Leu Glu Glu Glu Glu Glu Ala Tyr Gly Trp Met
            20                  25                  30
```

```
-continued

Asp Phe

<210> SEQ ID NO 103
<211> LENGTH: 35
<212> TYPE: PRT
<213> ORGANISM: Homo Sapiens

<400> SEQUENCE: 103

Gln Leu Gly Pro Gln Gly Pro Pro His Leu Val Ala Asp Pro Ser Lys
1               5                   10                  15

Lys Gln Gly Pro Trp Leu Glu Glu Glu Glu Ala Tyr Gly Trp Met
            20                  25                  30

Asp Phe Gly
        35

<210> SEQ ID NO 104
<211> LENGTH: 17
<212> TYPE: PRT
<213> ORGANISM: Homo sapiens

<400> SEQUENCE: 104

Gln Gly Pro Trp Leu Glu Glu Glu Glu Ala Tyr Gly Trp Met Asp
1               5                   10                  15

Phe

<210> SEQ ID NO 105
<211> LENGTH: 18
<212> TYPE: PRT
<213> ORGANISM: Homo sapiens

<400> SEQUENCE: 105

Gln Gly Pro Trp Leu Glu Glu Glu Glu Ala Tyr Gly Trp Met Asp
1               5                   10                  15

Phe Gly

<210> SEQ ID NO 106
<211> LENGTH: 6
<212> TYPE: PRT
<213> ORGANISM: Homo sapiens

<400> SEQUENCE: 106

Ser Ala Glu Asp Glu Asn
1               5
```